United States Patent
Gazzard et al.

(10) Patent No.: US 8,410,279 B2
(45) Date of Patent: Apr. 2, 2013

(54) SUBSTITUTED PYRROLES AND METHODS OF USE

(75) Inventors: Lewis J. Gazzard, Belmont, CA (US); Joseph Lyssikatos, Piedmont, CA (US)

(73) Assignee: Genentech, Inc., South San Francisco, CA (US)

( * ) Notice: Subject to any disclaimer, the term of this patent is extended or adjusted under 35 U.S.C. 154(b) by 63 days.

(21) Appl. No.: 12/997,070

(22) PCT Filed: Jun. 10, 2009

(86) PCT No.: PCT/US2009/003493
§ 371 (c)(1),
(2), (4) Date: Jan. 31, 2011

(87) PCT Pub. No.: WO2009/151599
PCT Pub. Date: Dec. 17, 2009

(65) Prior Publication Data
US 2011/0118320 A1    May 19, 2011

Related U.S. Application Data

(60) Provisional application No. 61/060,752, filed on Jun. 11, 2008, provisional application No. 61/104,618, filed on Oct. 10, 2008.

(51) Int. Cl.
*C07D 401/12* (2006.01)
*A61K 31/4462* (2006.01)
(52) U.S. Cl. ..................... 546/279.1; 514/326
(58) Field of Classification Search ............... 546/279.1; 514/326
See application file for complete search history.

(56) References Cited

FOREIGN PATENT DOCUMENTS
WO     2005/066163 A2     7/2005

OTHER PUBLICATIONS

Kubinyi (3D QSAR in Drug Design: Ligand-Protein Interactions and Molecular Similarity, vol. 2-3, Springer, 1998, 800 pages). TOC, pp. 243-244 provided.*
Janetka et al. (Bioorg. Med. Chem. Lett. 18 (2008) 4242-4248).*
Wermuth, The Practice of Medicinal Chemsitry, 2d ed. (2003), 768 pages. Chapters 9-10 provided.*
Zabludoff et al. (Mol. Cancer Ther., 2008, 7, 2955-2966).*
"International Search Report, Written Opinion, and International Preliminary Report on Patentability for PCT/US2009/003493".
Bartek and Lukas, "Chk1 and Chk2 kinases in checkpoint control and cancer" *Cancer Cell* 3(5) :421-9 (2003).
Bartek et al., "CHK2 kinase—a busy messenger" *Nat Rev Mol Cell Biol.* 2(12) :877-86 (2001).
Hartwell et al., "Checkpoints: controls that ensure the order of cell cycle events" *Science* 246(4930):629-34 (Nov. 1989).

* cited by examiner

*Primary Examiner* — Robert Havlin
(74) *Attorney, Agent, or Firm* — Vivien M. Banholzer

(57) ABSTRACT

The invention relates to substituted pyrrole compounds of Formula (I) which are useful as kinase inhibitors, more specifically useful as checkpoint kinase 1 (chk1) inhibitors, thus useful as cancer therapeutics. The invention also relates to compositions, more specifically pharmaceutical compositions comprising these compounds and methods of using the same to treat various forms of cancer and hyperproliferative disorders, as well as methods of using the compounds for in vitro, in situ, and in vivo diagnosis or treatment of mammalian cells, or associated pathological conditions.

11 Claims, No Drawings

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial sequence
<220> FEATURE:
<223> OTHER INFORMATION: sequence is synthesized

<400> SEQUENCE: 1

Lys Lys Lys Val Ser Arg Ser Gly Leu Tyr Arg Ser Pro Ser Met
1               5                   10                  15

Pro Glu Asn Leu Asn Arg Pro Arg
            20
```

SUBSTITUTED PYRROLES AND METHODS OF USE

CROSS-REFERENCE TO RELATED APPLICATIONS

This application is made under 35 U.S. §371 based on International Application PCT/US2009/003493 filed on Jun. 10, 2009, and claims the benefit of U.S. Provisional Application No. 61/060,752, filed Jun. 11, 2008 and U.S. Provisional Application No. 61/104,618, filed Oct. 10, 2008, the disclosures of which are incorporated herein by reference in their entirety.

BACKGROUND OF THE INVENTION

The invention relates to substituted pyrrole compounds which are useful as kinase inhibitors, more specifically useful as checkpoint kinase 1 (chk1) inhibitors, thus useful as cancer therapeutics. The invention also relates to compositions, more specifically pharmaceutical compositions comprising these compounds and methods of using the same to treat various forms of cancer and hyperproliferative disorders, as well as methods of using the compounds for in vitro, in situ, and in vivo diagnosis or treatment of mammalian cells, or associated pathological conditions.

Individual cells replicate by making an exact copy of their chromosomes, and then segregating these into separate cells. This cycle of DNA replication, chromosome separation and division is regulated by mechanisms within the cell that maintain the order of the steps and ensure that each step is precisely carried out. Involved in these processes are the cell cycle checkpoints (Hartwell et al., Science, Nov. 3, 1989, 246(4930):629-34) where cells may arrest to ensure DNA repair mechanisms have time to operate prior to continuing through the cycle into mitosis. There are two such checkpoints in the cell cycle—the G1/S checkpoint that is regulated by p53 and the G2/M checkpoint that is monitored by the serine/threonine kinase checkpoint kinase 1 (chk1).

Chk1 and Chk2 are structurally unrelated yet functionally overlapping serine/threonine kinases activated in response to genotoxic stimuli (reviewed in Bartek et al., Nat. Rev. Mol. Cell Biol. 2001, vol. 2, pp. 877-886). Chk1 and Chk2 relay the checkpoint signals from the ATM and ATR, which phosphorylate and activate them. Chk2 is a stable protein expressed throughout the cell cycle, activated mainly by ATM in response to double-strand DNA breaks (DSBs). In contrast, Chk1 protein expression is largely restricted to S and G2 phases. In response to DNA damage, ChK1 is phosphorylated and activated by ATM/ATR, resulting in cell cycle arrest in the S and G2/M phases to allow for repair of DNA damage (reviewed in Cancer Cell, Bartek and Lukas, Volume 3, Issue 5, May 2003, Pages 421-429. Inhibition of Chk1 has been shown to abrogate cell cycle arrest leading to enhanced tumor cell death following DNA damage by a range of chemotherapeutics. Cells lacking intact G1 checkpoints are particularly dependent on S and G2/M checkpoints and are therefore expected to be more sensitive to chemotherapeutic treatment in the presence of a chk1 inhibitor, whereas normal cells with functional G1 checkpoints would be predicted to undergo less cell death.

SUMMARY OF THE INVENTION

The invention relates generally to substituted pyrroles of Formula (I) (and/or solvates, hydrates, and/or salts thereof) with kinase inhibitory activity, more specifically with chk1 inhibitory activity. The compounds of the present invention are also useful as inhibitors of Glycogen Synthase Kinase-3 (GSK-3), KDR kinase, and FMS-like tyrosine kinase 3 (FLT3). Accordingly, the compounds of the invention and compositions thereof are useful in the treatment of hyperproliferative disorders such as cancer.

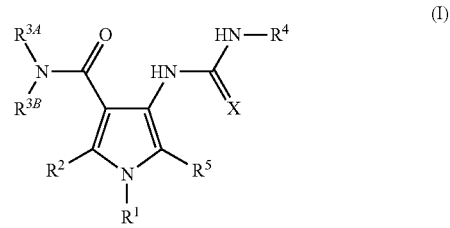

$R^1$ is phenyl or heteroaryl wherein said phenyl and heteroaryl is optionally substituted with one to five groups independently selected from halo, CN, $CF_3$, —$OCF_3$, —$NO_2$, —$C(O)OR^7$, —$C(O)NR^7R^8$, —$NR^7R^8$, —$OR^7$, —$S(O)_pR^7$, —$NR^8C(O)R^7$, —$NR^8C(O)OR^7$, —$NR^8C(O)NR^7R^8$, —$NR^8SO_2R^7$, —$OC(O)R^7$, —$OC(O)NR^7R^8$, —$S(O)_2NR^7R^8$, and $R^9$;

$R^2$ is H, chloro, fluoro, or CN;

$R^{3A}$ and $R^{3B}$ are independently H, alkyl, cycloalkyl, or heterocyclyl, wherein said alkyl, cycloalkyl, and heterocyclyl are optionally substituted with one to five groups independently selected from halo, CN, $CF_3$, —$OCF_3$, —$NO_2$, —$C(O)OR^7$, —$C(O)NR^7R^8$, —$NR^7R^8$, —$S(O)_pR^7$, —$NR^8C(O)R^7$, —$NR^8C(O)OR^7$, —$NR^8C(O)NR^7R^8$, —$NR^8SO_2R^7$, —$OC(O)R^7$, —$OC(O)NR^7R^8$, —$S(O)_2NR^7R^8$, and $R^9$;

$R^{3A}$ and $R^{3B}$ are optionally taken together with the attached N atom to form a 4-10 membered monocyclic or bicyclic ring having additional 0-2 heteroatoms selected from O, S, and N, said ring being optionally substituted with one to five groups independently selected from halo, CN, $CF_3$, —$OCF_3$, —$NO_2$, —$C(O)OR^7$, —$C(O)NR^7R^8$, —$NR^7R^8$, —$S(O)_pR^7$, —$NR^8C(O)R^7$, —$NR^8C(O)OR^7$, —$NR^8C(O)NR^7R^8$, —$NR^8SO_2R^7$, —$OC(O)R^7$, —$OC(O)NR^7R^8$, —$S(O)_2NR^7R^8$, and $R^9$;

X is O or $N(R^6)$;

$R^6$ is H, CN, or $C_1$-$C_2$ alkyl wherein said alkyl is optionally substituted with one or more groups selected from OH, $O(C_1$-$C_2$ alkyl), fluoro, and cyclopropyl;

$R^4$ is H, $C_1$-$C_3$ alkyl, $C_3$-$C_5$ cycloalkyl, or $(CH_2)_{0-1}$-4-5 membered heterocyclyl, wherein said alkyl is optionally substituted with one or more groups selected from OH, $O(C_1$-$C_2$ alkyl), fluoro and $C_3$-$C_5$ cycloalkyl, and said cycloalkyl is optionally substituted with OH;

$R^5$ is H, chloro, fluoro, or CN;

each p independently is 0, 1 or 2;

each occurrence of $R^7$ and $R^8$ is independently H, alkyl, cycloalkyl, heterocyclyl, aryl or heteroaryl, wherein said alkyl, cycloalkyl, heterocyclyl, aryl and heteroaryl are optionally substituted with one to five $R^{10}$ groups;

$R^7$ and $R^8$ are optionally taken together with the attached N atom to form a 4-7 membered ring having additional 0-2 heteroatoms selected from O, S, and N, said ring being optionally substituted with one to five $R^{10}$ groups;

$R^9$ is independently alkyl, cycloalkyl, heterocyclyl, aryl or heteroaryl, wherein said alkyl, cycloalkyl, heterocyclyl, aryl and heteroaryl are optionally substituted with one to five $R^{10}$ groups;

each $R^{10}$ is independently halo, CN, $CF_3$, —$OCF_3$, —$NO_2$, —C(O)$OR^{11}$, —C(O)$NR^{11}R^{12}$, —$NR^{11}R^{12}$, —$OR^{11}$, —S(O)$_pR^{11}$, —$NR^{12}$C(O)$R^{11}$, —$NR^{12}$C(O)$OR^{11}$, —$NR^{12}$C(O)$NR^{11}R^{12}$, —$NR^{12}SO_2R^{11}$, —OC(O)$R^{11}$, —OC(O)$NR^{11}R^{12}$; —S(O)$_2NR^{11}R^{12}$; or $R^{13}$;

each occurrence of $R^{11}$ and $R^{12}$ is independently selected from H, alkyl, cycloalkyl, heterocyclyl, aryl or heteroaryl, wherein said alkyl, cycloalkyl, heterocyclyl, aryl and heteroaryl are optionally substituted with one to five $R^{14}$ groups;

$R^{11}$ and $R^{12}$ are optionally taken together with the attached N atom to form a 5-6 membered ring having additional 0-2 heteroatoms selected from O, S, and N, said ring being optionally substituted with one to five $R^{14}$ groups;

$R^{13}$ is independently alkyl, cycloalkyl, heterocyclyl, aryl or heteroaryl, wherein said alkyl, cycloalkyl, heterocyclyl, aryl and heteroaryl are optionally substituted with one to five $R^{14}$ groups;

each $R^{14}$ is independently halo, CN, $CF_3$, —$OCF_3$, —$NO_2$, —C(O)$OR^{15}$, —C(O)$NR^{15}R^{16}$, —$NR^{15}R^{16}$, —$OR^{15}$, —S(O)$_pR^{15}$, —$NR^{16}$C(O)$R^{15}$, —$NR^{16}$C(O)$OR^{15}$, —$NR^{16}$C(O)$NR^{15}R^{16}$, —$NR^{16}SO_2R^{15}$, —OC(O)$R^{15}$, —OC(O)$NR^{15}R^{16}$, —S(O)$_2NR^{15}R^{16}$, or $R^{17}$;

each occurrence of $R^{15}$ and $R^{16}$ is independently H, alkyl, cycloalkyl, heterocyclyl, aryl, or heteroaryl, wherein said alkyl, cycloalkyl, heterocyclyl, aryl, and heteroaryl are optionally substituted with one to four groups selected from halo, —CN, —$OCF_3$, —$CF_3$, —$NO_2$, —$C_1$-$C_6$ alkyl, —OH, oxo, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$ ($C_1$-$C_6$ alkyl), —$CO_2$H, —$CO_2$($C_1$-$C_6$ alkyl), —C(O)$NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —$SO_2NH_2$, —$SO_2$NH($C_1$-$C_6$ alkyl), —$SO_2$N ($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C(O)NH ($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O ($C_1$-$C_6$ alkyl);

$R^{15}$ and $R^{16}$ are optionally taken together with the attached N atom to form a 5-6 membered ring having additional 0-2 heteroatoms selected from O, S, and N, said ring being optionally substituted with one to four groups selected from halo, —CN, —$OCF_3$, —$CF_3$, —$NO_2$, —$C_1$-$C_6$ alkyl, —OH, oxo, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$ ($C_1$-$C_6$ alkyl), —$CO_2$H, —$CO_2$($C_1$-$C_6$ alkyl), —C(O) $NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —$SO_2NH_2$, —$SO_2$NH($C_1$-$C_6$ alkyl), —$SO_2$N ($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C(O)NH ($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O ($C_1$-$C_6$ alkyl); and $R^{17}$ is alkyl, cycloalkyl, heterocyclyl, aryl, or heteroaryl, wherein said alkyl, cycloalkyl, heterocyclyl, aryl and heteroaryl are optionally substituted with one to four groups selected from halo, —CN, —$OCF_3$, —$CF_3$, —$NO_2$, —$C_1$-$C_6$ alkyl, —OH, oxo, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$($C_1$-$C_6$ alkyl), —$CO_2$H, —$CO_2$ ($C_1$-$C_6$ alkyl), —C(O)$NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O) ($C_1$-$C_6$ alkyl), —NHSO$_2$($C_1$-$C_6$ alkyl), —N($C_1$-$C_6$ alkyl) SO$_2$($C_1$-$C_6$ alkyl), —$SO_2NH_2$, —$SO_2$NH($C_1$-$C_6$ alkyl), —$SO_2$N($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C (O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl) C(O)O($C_1$-$C_6$ alkyl).

The present invention includes a composition (e.g., a pharmaceutical composition) comprising a compound of Formula (I) (and/or solvates, hydrates and/or salts thereof) and a carrier (a pharmaceutically acceptable carrier). The present invention also includes a composition (e.g., a pharmaceutical composition) comprising a compound of Formula (I) (and/or solvates, hydrates and/or salts thereof) and a carrier (a pharmaceutically acceptable carrier), further comprising a second chemotherapeutic agent. The present compositions are therefore useful for inhibiting abnormal cell growth or treating a hyperproliferative disorder in a mammal (e.g., human), such as cancer.

The present invention includes a method of inhibiting abnormal cell growth or treating a hyperproliferative disorder in a mammal (e.g., human) such as cancer comprising administering to said mammal a therapeutically effective amount of a compound of Formula (I) (and/or solvates, hydrates and/or salts thereof) or a composition thereof, alone or in combination with a second chemotherapeutic agent.

The present invention includes a method of using the present compounds for in vitro, in situ, and in vivo diagnosis or treatment of mammalian cells, organisms, or associated pathological conditions.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are, not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2$CH($CH_3$)$_2$), 2-butyl (s-Bu, s-butyl, —CH($CH_3$) $CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The term "cycloalkyl" refers to a monovalent non-aromatic, saturated or partially unsaturated ring having 3 to 12 carbon atoms as a monocyclic ring or 6 to 12 carbon atoms as a bicyclic ring. Bicyclic carbocycles having 6 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-14 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like.

The terms "heterocycle," "heterocyclyl" and "heterocyclic ring" are used interchangeably herein and refer to a saturated or a partially unsaturated (i.e., having one or more double bonds within the ring) carbocyclic radical of 3 to 14 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, and S) or a bicycle having 6 to 10 ring members (4 to 9 carbon atoms and 1 to 6 heteroatoms selected from N, O, and S), for example: a bicyclo [4,5], [5,5], [5,6], or [6,6] system or a bridged [2.1.1], [2.2.1], [2.2.2] or [3.2.2] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydropyranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-16 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, tetrahydrothiophene, thiophene, pyrrole or pyrrolidine, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-oxo-1,2-dihydropyridine, or 4-oxo-1,4-dihydropyridine; position 2 of a isoindole, or isoindoline; position 4 of a morpholine; and position 9 of a carbazole, or β-carboline.

The term "halo" refers to F, Cl, Br or I. The heteroatoms present in heteroaryl or heterocyclyl include the oxidized forms such as N$^+$→O$^-$, S(O) and S(O)$_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms. This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Tumors include solid and liquid tumors. Examples of cancer include, but are not limited to, carcinoma, lymphoma, blastoma, sarcoma, myeloma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, malignant brain tumors, melanoma, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, as well as acute myelogenous leukemia (AML).

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; bestrabucil; bisantrene; edatraxate; defofamine; demecolcine; diaziquone; elformithine; elliptinium acetate; an epothilone; etoglucid; gallium nitrate; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); chloranmbucil; 6-thioguanine; mercaptopurine; ifosfamide; mitoxantrone; novantrone; edatrexate; daunomycin; aminopterin; capecitabine (XE-LODA®); ibandronate; CPT-11; difluoromethylornithine (DMFO); and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Other examples of "chemotherapeutic agents" that can be used in combination with the present compounds include inhibitors of MEK (MAP kinase kinase), such as XL518 (Exelixis, Inc.) and AZD6244 (Astrazeneca); inhibitors of Raf, such as XL281 (Exelixis, Inc.), PLX4032 (Plexxikon), and ISIS5132 (Isis Pharmaceuticals); inhibitors of mTor (mammalian target of rapamycin), such as rapamycin, AP23573 (Ariad Pharmaceuticals), temsirolimus (Wyeth Pharmaceuticals) and RAD001 (Novartis); inhibitors of PI3K (phosphoinositide-3 kinase), such as SF-1126 (PI3K inhibitor, Semafore Pharmaceuticals), BEZ-235 (PI3K inhibitor, Novartis), XL-147 (PI3K inhibitor, Exelixis, Inc.), and GDC-0941 (Genentech); inhibitors of cMet, such as PHA665752 (Pfizer), XL-880 (Exelixis, Inc.), ARQ-197 (ArQule), and CE-355621; and pharmaceutically acceptable salts, acids and derivatives of any of the above.

Examples of a "chemotherapeutic agent" also include a DNA damaging agent such as thiotepa and CYTOXAN® cyclosphosphamide; alkylating agents (for example cis-platin; carboplatin; cyclophosphamide; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; busulphan; nitrosoureas such as carmustine, chlorozotocin, fotemustine, lomustine, nimustine, and ranimnustine; and temozolomide); antimetabolites (for example antifolates such as fluoropyrimidines like 5-fluorouracil (5-FU) and tegafur, raltitrexed, methotrexate, cytosine arabinoside, hydroxyurea and GEMZAR® (gemcitabine); antitumour antibiotics such as the enediyne antibiotics (e.g., calicheamicin, especially calicheamicin gamma1I and calicheamicin omega1I (Angew Chem. Intl. Ed. Engl. (1994) 33:183-186); anthracyclines like adriamycin; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; antimitotic agents (for example vinca alkaloids like vincristine, vinblastine, vindesine and NAVELBINE® (vinorelbine) and taxoids like taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); topoisomerase inhibitors (for example RFS 2000, epipodophyllotoxins like etoposide and teniposide, amsacrine, a camptothecin (including the synthetic analog topotecan), and irinotecan and SN-38) and cytodifferentiating agents (for example retinoids such as all-trans retinoic acid, 13-cis retinoic acid and fenretinide); and pharmaceutically acceptable salts, acids and derivatives of any of the above.

A "chemotherapeutic agent" also includes an agent that modulates the apoptotic response including inhibitors of IAP (inhibitor of apoptosis proteins) such as AEG40826 (Aegera Therapeutics); and inhibitors of bcl-2 such as GX15-070 (Gemin X Biotechnologies), CNDO103 (Apogossypol; Coronado Biosciences), HA14-1 (ethyl 2-amino-6-bromo-4-(1-cyano-2-ethoxy-2-oxoethyl)-4H-chromene-3-carboxylate), AT101 (Ascenta Therapeutics), ABT-737 and ABT-263 (Abbott); and pharmaceutically acceptable salts, acids and derivatives of any of the above.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as chk inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. For example, any reference to a structure of 2-hydroxypyridine include its tautomer 2-oxo-1,2-dihydropyridine, also known as 2-pyridone, and vice versa.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, methanesulfonic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ), 2-(trimethylsilyl) ethoxymethyl (SEM) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and t-butyldimethylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula (I)", unless otherwise indicated, include compounds of Formula I and stereoisomers, geometric isomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula (I), wherein one or more hydrogen atoms are replaced deuterium or tritium, or one or more carbon atoms are replaced by a $^{13}$C- or $^{14}$C-enriched carbon are within the scope of this invention.

The present invention provides substituted pyrroles of Formula (I) (and/or solvates, hydrates and/or salts thereof) as described above with kinase inhibitory activity, such as chk1, chk2, GSK-3, KDR and/or FLT3 inhibitory activities. The present compounds are particularly useful as chk1 kinase inhibitors.

In certain embodiments of the present invention, $R^1$ is phenyl substituted with one to three groups independently selected from halo, CN, $CF_3$, $-OCF_3$, $-NO_2$, $-C(O)OR^7$, $-C(O)NR^7R^8$, $-NR^7R^8$, $-OR^7$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I). In certain embodiments of the present invention, $R^1$ is phenyl substituted with one to three groups independently selected from halo, CN, and $CF_3$; and all other variables are as defined in Formula (I).

In certain embodiments of the present invention, $R^2$ is H; and all other variables are as defined in Formula (I), or as defined in any one of the embodiments above.

In certain embodiments of the present invention, $R^{3A}$ is H; and all other variables are as defined in Formula (I), or as defined in any one of the embodiments above.

In certain embodiments of the present invention, $R^{3B}$ is H, cycloalkyl or heterocyclyl, wherein said cycloalkyl and heterocyclyl are optionally substituted with one to three groups independently selected from halo, CN, $CF_3$, $-OCF_3$, $-NO_2$, $-C(O)OR^7$, $-C(O)NR^7R^8$, $-NR^7R^8$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I), or as defined in any one of the embodiments above.

In certain embodiments of the present invention, $R^{3B}$ is cycloalkyl optionally substituted with one to three groups independently selected from halo, CN, $CF_3$, $-OCF_3$, $-NO_2$, $-C(O)OR^7$, $-C(O)NR^7R^8$, $-NR^7R^8$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I), or as defined in any one of the embodiments above. In certain embodiments of the present invention, $R^{3B}$ is cycloalkyl optionally substituted with $-NR^7R^8$; and all other variables are as defined in Formula (I), or as defined in any one of the embodiments above.

In certain embodiments of the present invention, $R^{3B}$ is 4-7 membered monocyclic or 8-10 membered bicyclic saturated heterocyclyl, wherein said heterocyclyl is optionally substituted with one to three groups independently selected from halo, CN, $CF_3$, $-NO_2$, $-C(O)OR^7$, $-C(O)NR^7R^8$, $-NR^7R^8$, $-OR^7$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I), or as defined in any one of the embodiments above.

In certain embodiments of the present invention, $R^{3B}$ is piperidinyl, pyrrolidinyl, azepanyl, or azetidinyl, wherein said piperidinyl, pyrrolidinyl, azepanyl, or azetidinyl is optionally substituted with one to three groups independently selected from halo, CN, $CF_3$, $-OCF_3$, $-NO_2$, $-C(O)OR^7$, $-C(O)NR^7R^8$, $-NR^7R^8$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I), or as defined in any one of the embodiments above. In certain embodiments of the present invention, $R^{3B}$ is piperidinyl; and all other variables are as defined in Formula (I), or as defined in any one of the embodiments above.

In certain embodiments of the present invention, $R^{3A}$ and $R^{3B}$ are optionally taken together with the attached N atom to form a 4-10 membered monocyclic or bicyclic ring having additional 0-2 heteroatoms selected from O, S, and N, said ring being optionally substituted with one to five groups independently selected from halo, CN, $CF_3$, $-OCF_3$, $-NO_2$, $-C(O)OR^7$, $-C(O)NR^7R^8$, $-NR^7R^8$, $-OR^7$, $-S(O)_pR^7$, $-NR^8C(O)R^7$, $-NR^8C(O)OR^7$, $-NR^8C(O)NR^7R^8$, $-NR^8SO_2R^7$, $-OC(O)R^7$, $-OC(O)NR^7R^8$, $-S(O)_2NR^7R^8$, and $R^9$; and all other variables are as defined in Formula (I), or as defined in any one of the embodiments above.

In certain embodiments of the present invention, X is O; and all other variables are as defined in Formula (I), or as defined in any one of the embodiments above. In certain embodiments of the present invention, X is $N(R^6)$ and $R^6$ is H, or CN; and all other variables are as defined in Formula (I), or as defined in any one of the embodiments above.

In certain embodiments of the present invention, $R^4$ is H, $CH_3$, $CH_2CH_3$, n-propyl, i-propyl, $CH_2CH_2OH$, $CH_2CH_2OCH_3$, $CH_2CH_2CH_2OH$, $CH_2CH_2CH_2OCH_3$, cyclopropyl, $CH_2$-cyclopropyl, $CH_2CH_2F$, $CH_2CHF_2$, or $CH_2CF_3$; and all other variables are as defined in Formula (I), or as defined in any one of the embodiments above. In certain embodiments of the present invention, $R^4$ is cyclobutyl, N-3-oxetanyl, (2-oxetanyl)methyl, (3-oxetanyl)methyl, (2-tetrahydrofuranyl)methyl, or (3-tetrahydrofuranyl)methyl; and all other variables are as defined in Formula (I), or as defined in any one of the embodiments above.

In certain embodiments of the present invention, $R^5$ is H; and all other variables are as defined in Formula (I), or as defined in any one of the embodiments above.

Another embodiment of the present invention includes title compounds described in EXAMPLES 1-21.

The present compounds are prepared according to the procedures described in the schemes below or by methods known in the art. The starting materials may be obtained from commercial sources, prepared from commercially available compounds, or prepared using known synthetic methods.

For example, N-aryl pyrroles of formula (1-9), (2-6), (3-3) or (4-12) may be prepared using the synthetic routes outlined in Schemes 1-4.

Scheme 1

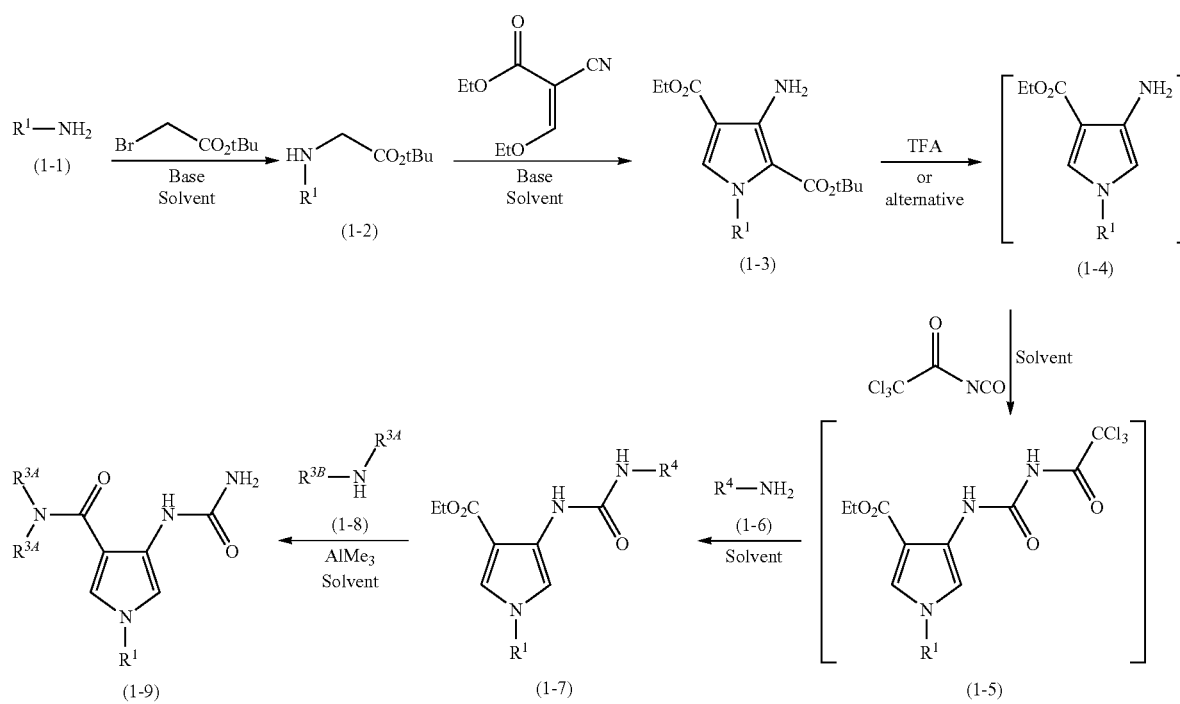

Compounds of formula (1-1) can be obtained from commercial sources, prepared from commercially available compounds, or prepared using well known synthetic methods. They may be reacted with an alpha-haloacetate, such as tert-butyl bromoacetate, in the presence of a base, such as triethylamine or N,N-diisopropylamine, with the optional addition of a phase transfer catalyst, such as tert-butylammonium iodide, in a suitable solvent, such as THF, acetonitrile or N,N-dimethylformamide, at a temperature between room temperature and 65° C., to obtain compounds of formula (1-2).

Compounds of formula (1-2) may be converted to compounds of formula (1-3) by reaction with an alkoxyacrylonitrile, such as ethyl(ethoxymethylene)cyanoacetate, in the presence of a base, such as 1,8-diazabicyclo[5.4.0]undec-7-ene, in a suitable solvent such as toluene, at a temperature between room temperature and 120° C.

Compounds of formula (1-4) may be obtained from compounds of formula (1-3) by reaction with trifluoroacetic acid, with the optional addition of a suitable solvent such as dichloromethane, at a temperature between room temperature and the reflux temperature of the solvent. Alternatively, compounds of formula (1-4) may be obtained from compounds of formula (1-3) by reaction with an acid, such as 0.5-6.0 N hydrochloric acid, in a suitable solvent, such as 1,4-dioxane, at a temperature between room temperature and the reflux temperature of the solvent.

Compounds of formula (1-5) can be obtained from compounds of formula (1-4) by reaction with trichloroacetyl isocyanate, in a suitable solvent, such as tetrahydrofuran, N,N-dimethylformamide, or dichloromethane, at a temperature between 0° C. and room temperature.

Intermediates of formula (1-5) can be reacted with an amine (1-6), such as ammonia, in a suitable solvent, such as methanol, at a temperature between 0° C. and room temperature, to obtain the compounds of formula (1-7).

Compounds of formula (VI) (1-7) can be reacted with an amine (1-8), such as (S)-(+)-3-amino-1-Boc-piperidine, in the presence of a Lewis acid, such as trimethylaluminium, in an inert solvent, such as tetrahydrofuran, at a temperature between room temperature and 65° C. It is to be understood that if compounds of formula (1-7) or (1-8) contain a protecting group, it may be necessary to deprotect the resultant products to yield compounds of formula (1-9), or salts thereof, which can then be converted into the corresponding free base or other pharmaceutically acceptable salts by standard methods.

N-Aryl pyrroles of formula (2-6) may be prepared using the synthetic routes outlined in Scheme 2.

Scheme 2

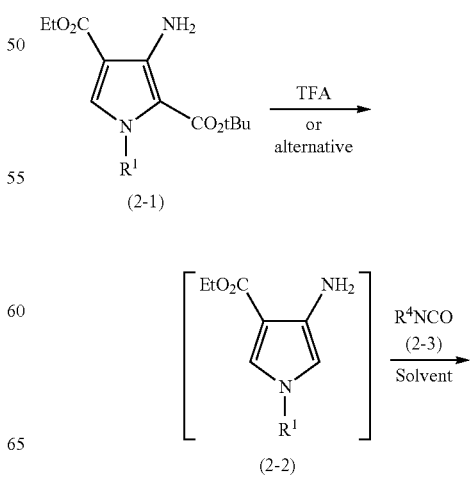

17
-continued

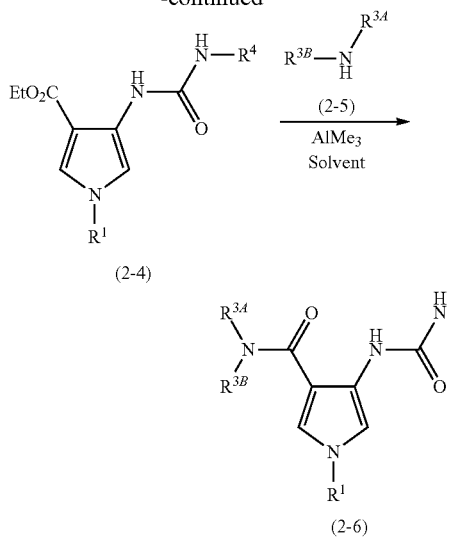

(2-4)

(2-6)

Compounds of formula (2-1) and intermediates of formula (2-2) may be prepared using the synthetic routes outlined in Scheme 1.

Intermediates of formula (2-4) may be prepared by treatment of intermediate (2-2) with an alkyl isocyanate (2-3), in a suitable solvent such as THF or diethyl ether, at a temperature between 0° C. and room temperature.

Compounds of formula (2-4) can be reacted with an amine (2-5), such as (S)-(+)-3-amino-1-Boc-piperidine, in the presence of a Lewis acid, such as trimethylaluminium, in an inert solvent, such as tetrahydrofuran, at a temperature between room temperature and 65° C. The resultant products may require deprotection to yield compounds of formula (2-6), or pharmaceutically acceptable salts thereof.

18

N-Aryl pyrroles of formula (3-3) may be prepared using the synthetic routes outlined in Scheme 3.

Scheme 3

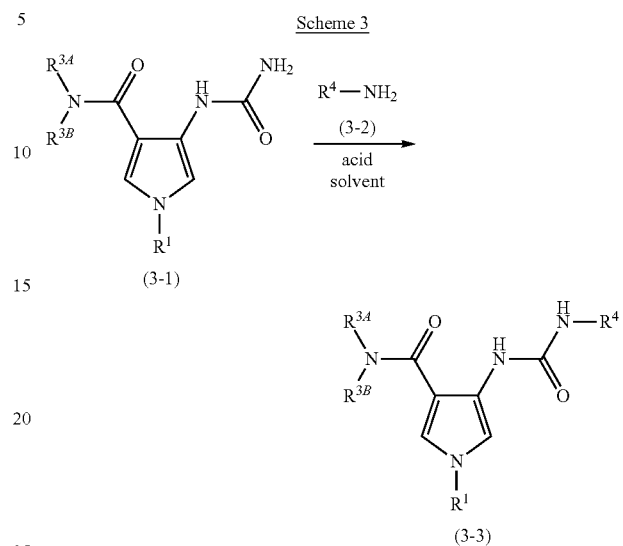

Intermediates of formula (3-1) may be reacted with an amine (3-2), such as 2-methoxyethylamine or cyclopropanemethylamine in the presence of an acid, such as acetic acid, in a suitable high-boiling solvent such as toluene, at a temperature between 100° C. and 150° C. The resultant products may require deprotection to yield compounds of formula (3-3), or pharmaceutically acceptable salts thereof.

N-Aryl pyrroles of formula (4-13) may be prepared using the synthetic routes outlined in Scheme 4.

Scheme 4

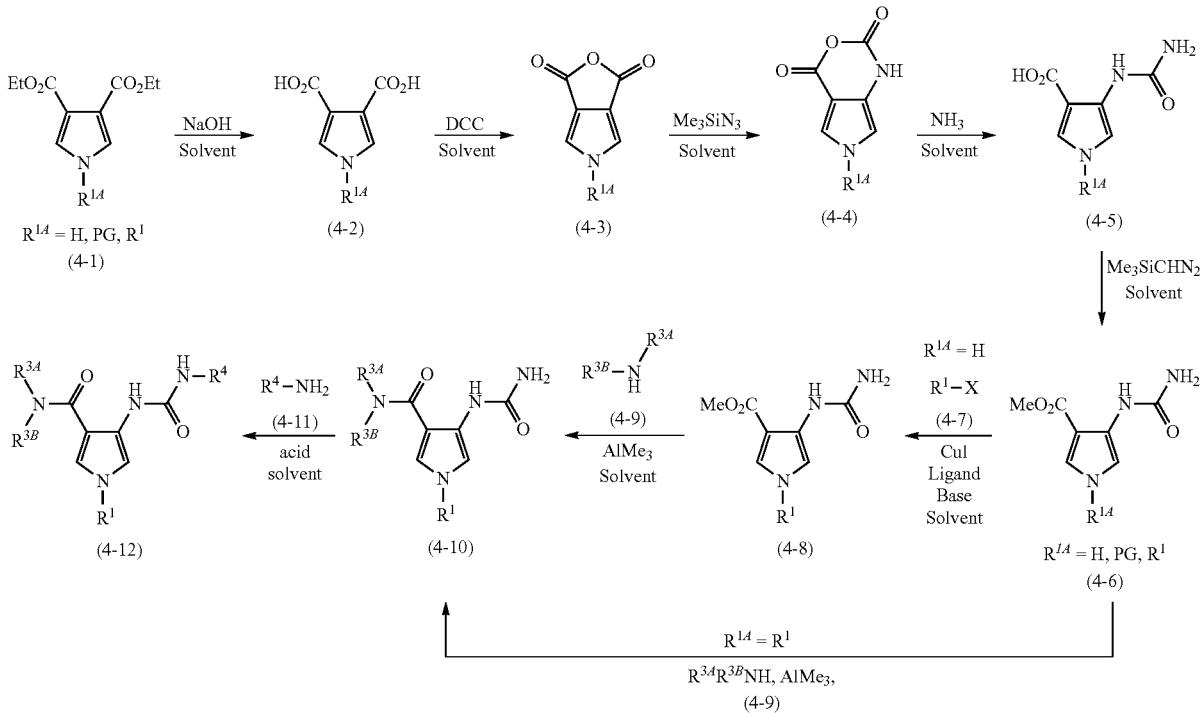

$R^{3A}R^{3B}NH$, $AlMe_3$,
(4-9)

Compounds of formula (4-1) can be obtained from commercial sources, prepared from commercially available compounds, or prepared using well known synthetic methods. Compounds of formula (4-2) may be may be prepared by reacting compounds of formula (4-1) with a base, such as sodium hydroxide or potassium hydroxide, in a suitable solvent, such as methanol or ethanol, at a temperature between room temperature and 85° C.

Compounds of formula (4-2) may be converted to compounds of formula (4-3) by reaction with a dehydrating agent, such as N,N-dicyclohexylcarbodiimide, in a suitable solvent such as acetonitrile or THF, at a temperature between room temperature and 50° C.

Compounds of formula (4-4) may be obtained from compounds of formula (4-3) by reaction with trimethylsilyl azide, in a suitable solvent such as acetonitrile or THF, at a temperature between room temperature and the reflux temperature of the solvent.

Compounds of formula (4-4) can be converted to compounds of formula (4-5) by reaction with ammonia, in a suitable solvent, such as dioxane or THF, with the optional addition of a co-solvent, such as N,N-dimethylformamide, at a temperature between room temperature and the reflux temperature of the solvent.

Compounds of formula (4-6) may be obtained from compounds of formula (4-5) by reaction with trimethylsilyl diazomethane, in a suitable solvent, such as THF with methanol, at a temperature between room temperature and the reflux temperature of the solvent.

Compounds of formula (4-6), where $R^{1A}$ is PG (protecting group), can be converted to compounds of formula (4-6), where $R^{1A}$ is H, where $R^5$=H, using standard deprotection methods as described above. Compounds of formula (4-6), where $R^{1A}$=H, can be converted to compounds of formula (4-8) by reaction with an aryl halide or heteroaryl halide (4-7), in the presence of a suitable catalyst, such as copper (I) bromide or copper (I) iodide, with optional use of a ligand, such as trans-N,N-dimethyl-1,2-cyclohexanediamine or 1,10-phenanthroline, in the presence of a suitable base, such as potassium phosphate, in a suitable solvent, such as N,N-dimethylformamide or toluene, at a temperature between room temperature and the reflux temperature of the solvent.

Compounds of formula (4-10) may be obtained from compounds of formula (4-6), where $R^{1A}$ is $R^1$, or from compounds of formula (4-8) by reaction with an amine (4-9), such as (S)-(+)-3-amino-1-Boc-piperidine, in the presence of a Lewis acid, such as trimethylaluminium, in an inert solvent, such as tetrahydrofuran, at a temperature between room temperature and 65° C.

Intermediates of formula (4-10) may be reacted with an amine (4-11), in the presence of an acid, such as acetic acid, in a suitable high-boiling solvent such as toluene, at a temperature between 100° C. and 150° C. The resultant products may require deprotection to yield compounds of formula (4-12), or pharmaceutically acceptable salts thereof.

It will be appreciated that where appropriate functional groups exist, compounds of formula (1-9), (2-6), (3-3), or (4-12), or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

In a further example primary amine (—$NH_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—$NHSO_2R'$ or —$NR''SO_2R'$) groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N=C=O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalysed hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit chk1 activity and activation (primary assays) and for their biological effects on growing cells (secondary assays) as described below. The compounds having $IC_{50}$ of less than 10 µM (more preferably less than 5 µM, even more preferably less than 1 µM, most preferably less than 0.5 µM) in the chk1 activity and activation assay of Example i, and $EC_{50}$ of less than 10 µM (more preferably less than 5 µM, most preferably less than 1 µM) in the cellular assay of Example ii, are useful as chk1 inhibitors.

The present invention includes a composition (e.g., a pharmaceutical composition) comprising a compound of Formula (I) (and/or solvates, hydrates and/or salts thereof) and a carrier (a pharmaceutically acceptable carrier). The present invention also includes a composition (e.g., a pharmaceutical composition) comprising a compound of Formula (I) (and/or solvates, hydrates and/or salts thereof) and a carrier (a pharmaceutically acceptable carrier), further comprising a second chemotherapeutic agent such as those described herein. The present invention also includes a composition (e.g., a pharmaceutical composition) comprising a compound of Formula (I) (and/or solvates, hydrates and/or salts thereof) and a carrier (a pharmaceutically acceptable carrier), further comprising a second chemotherapeutic agent such as a DNA damaging agent including those described herein. The present compositions are useful for inhibiting abnormal cell growth or treating a hyperproliferative disorder such as cancer in a mammal (e.g., human). For example, the present compounds and compositions are useful for treating breast cancer, colorectal cancer, ovarian cancer, non-small cell lung cancer, malignant brain tumors, sarcomas, melanoma, lymphoma, myelomas and/or leukemia in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula (I) (and/or solvates, hydrates and/or salts thereof) or a composition thereof. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I) (and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula (I) (and/or solvates, hydrates and/or salts thereof) or a composition thereof, in combination with a second chemotherapeutic agent such as those described herein. The present invention also includes a method of inhibiting abnormal cell growth or treating a hyperproliferative disorder such as cancer in a mammal (e.g., human) comprising administering to said mammal a therapeutically effective amount of a compound of Formula (I) (and/or solvates, hydrates and/or salts thereof) or a composition thereof, in combination with a second chemotherapeutic agent such as a DNA damaging agent including those described herein. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I) (and/or solvates, hydrates and/or salts thereof) or a composition thereof, in combination with a second chemotherapeutic agent such as those described herein. the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I) (and/or solvates, hydrates and/or salts thereof) or a composition thereof, in combination with a second chemotherapeutic agent such as a DNA damaging agent including those described herein.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

| Abbreviations | |
|---|---|
| ATP | Adenosine-5'-triphosphate |
| DCM | Dichloromethane |
| DIPEA | Diisopropylethylamine |
| DMF | Dimethylformamide |
| DMSO | Dimethylsulfoxide |
| DMSO-$D_6$ | Deuterated dimethylsulfoxide |
| Eq. | Equivalents |
| EtOAc | Ethyl acetate |
| h | Hour |
| HCl | Hydrochloric acid |
| HM-N | Isolute ® HM-N is a modified form of diatomaceous earth that can efficiently adsorb organic samples |
| mmol | Millimoles |
| mol | Moles |
| LCMS | Liquid Chromatography Mass Spectroscopy |
| MeOH | Methanol |
| MeOH-$D_4$ | Deuterated Methanol |
| MeCN | Acetonitrile |
| N | Normal (concentration) |
| NMR | Nuclear magnetic resonance |
| $NaHCO_3$ | Sodium bicarbonate |
| SCX-II | Pre-packed Isolute ® silica-based cartridge with a chemically bonded propylsulfonic acid functional group |
| Si-SPE | Pre-packed Isolute ® silica flash chromatography cartridge |
| Si-ISCO | Pre-packed ISCO ® silica flash chromatography cartridge |
| TBAI | tert-Butyl ammonium iodide |
| TLC | Thin layer chromatography |
| TFA | Trifluoroacetic acid |
| THF | Tetrahydrofuran |
| Rochelle's salt | Potassium sodium L-tartrate tetrahydrate |

General Experimental Conditions $^1$H NMR spectra were recorded at ambient temperature using a Varian Unity Inova (400 MHz) spectrometer with a triple resonance 5 mm probe or a Bruker Avance DPX (300 MHz) spectrometer with a dual resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP 1100 LC system with diode array detector. This system uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Microwave experiments were carried out using a Biotage Initiator 60™ which uses a single-mode resonator and dynamic field tuning. Temperature from 40-250° C. can be achieved, and pressures of up to 30 bar can be reached.

Example i

Chk1 and Chk2 Assays (Chk Primary Assays)

Full length human mutant recombinant protein, histidine tagged and expressed in insect cells is used as source of enzymatic activity (Invitrogen, chk1 from product PV3982 and Chk2 from product PV3983).

The chk1 AlphaScreen assay is carried out for 30 minutes in the presence of 10 μM ATP using biotinylated Akt substrate-1 peptide (Cell Signalling Technology, product #1065) as a substrate. Phosphorylation of the substrate is detected and quantified using AlphaScreen technology. This consists of an anti-phospho-Akt substrate-1 antibody (Cell Signalling technology Product #9611) and two AlphaScreen beads (Perkin Elmer), one product coated with Protein A which binds the antibody Ig chain (Product 6760137), and one coated with Streptavidin which binds the biotin on the biotinylated Akt substrate peptide-1 (Product 6760002). Chk1 activity results in the production of phosphorylated Akt substrate peptide-1 an event which causes the two bead species to be brought into close proximity in the presence of antibody leading to the generation of luminescence which is detected on a Perkin Elmer reader (Fusion).

The ATP Radiometric ChK1 assay is carried out by incubation for 30 minutes in the presence of 10 μM ATP containing 0.3 μCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

The chk2 AlphaScreen assay is carried out for 30 minutes in the presence of 30 μM ATP using biotinylated tyrosine hydroxylase (ser 40) peptide (Cell Signalling Technology, product #1132) as a substrate. Phosphorylation of the substrate is detected and quantified using AlphaScreen technology. This consists of an anti-phospho-tyrosine hydroxylase (ser 40) peptide antibody (Cell Signalling technology Product #2791) and two AlphaScreen beads (Perkin Elmer), one product coated with Protein A which binds the antibody Ig chain (Product 6760137), and one coated with Streptavidin which binds the biotin on the biotinylated tyrosine hydroxylase (ser 40) peptide (Product 6760002). Chk2 activity results in the production of phosphorylated tyrosine hydroxylase peptide an event which causes the two bead species to be brought into close proximity in the presence of antibody leading to the generation of luminescence which is detected on a Perkin Elmer reader (Fusion).

The ATP radiometric ChK2 assay is carried out by incubation for 30 minutes in the presence of 30 μM ATP containing 0.3 μCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

Test compounds are diluted in DMSO prior to addition to assay buffer, the final DMSO concentration in the assay is 1%.

The $IC_{50}$ is defined as the concentration at which a given test compound achieved 50% inhibition of the control. $IC_{50}$ values are calculated using the XLfit software package (version 2.0.5).

Tested title compounds of EXAMPLES 1-21 exhibited an $IC_{50}$ of less than 5 μM in the assays described in EXAMPLE i against chk1.

Example ii

Cellular Assay (Checkpoint Abrogation)

Compounds are tested in a cellular assay using the human colorectal adenocarcinoma derived cell line HT-29 (ATCC HTB-38).

The cell line is maintained in DMEM/F12 (1:1) media (Invitrogen Gibco, #31331) supplemented with 10% FCS at 37° C. in a 5% $CO_2$ humidified incubator.

Cells are seeded in 96-well plates at 30,000 cells/well and after 24 h they are exposed to 20 nM SN-38 in 0.4% DMSO. One column of 8 wells on each plate was used to generate a maximum signal control. These cells are treated with 0.4% DMSO without SN-38. Cells are grown for a further 16 h, then the media containing DMSO plus or minus SN-38 is removed and replaced with media containing 300 nM nocodazole alone (to determine baseline) or in combination with ten concentrations of chk1 inhibitor (final DMSO concentration is 0.4%). Cells are grown for a further 24 h. The media is removed and replaced with 50 μl lysis buffer containing protease inhibitors and phosphatase inhibitors. This buffer contains detergent to bring about cellular disruption. Following complete cellular disruption, 25 μl lysate is transferred to a MesoScale 96 well 4-spot plate coated with an antibody to Histone H3 (MesoScale Discovery (MSD) Product K110EWA-3) which have been previously blocked with 3% bovine serum albumin in Tris buffered saline. Following the transfer of lysate to the MSD plate, Histone H3 in the lysate is captured on the coated antibody by incubation at room temperature for 2 h. Following the capture step the plate is washed and then incubated with an antibody to phosphorylated Histone H3 which is conjugated with a Sulfo-Tag. This tag gives a signal when in proximity to the electrode on the base of the MSD plate. Binding the tagged antibody to the captured protein allow detection on a MSD reader.

The $EC_{50}$ is defined as the concentration at which a given compound achieves 50% decrease of the measured levels of phospho-Histone H3 within the range of a normal sigmoidal dose response curve compared to the signal generated by 300 nM nocodazole alone. $EC_{50}$ values are calculated using the XLfit software package (version 2.0.5) or Graphpad Prism, (version 3.03) fitting a sigmoidal curve with a variable slope.

Tested title compounds of EXAMPLES 1-21 exhibited an $EC_{50}$ of less than 10 μM in the assay described in EXAMPLE ii.

Synthesis of Pyrroles

General Method 1: Preparation of (4-arylamino)-acetic acid tert-butyl esters To a solution of aniline (10.4-90.1 mmol, 1.0 eq.), TBAI (0.20 eq.) and DIPEA (1.05 eq.) in dry THF was added tert-butylbromoacetate (1.01-1.05 eq.). The reaction mixture was stirred at a temperature between room temperature and 65° C., under a nitrogen atmosphere, for a period of 16-64 hours. The reaction mixture was then partitioned between EtOAc or DCM and water. The organic phase was washed with water, brine, dried, and concentrated. The resultant residue was then purified by flash chromatography (silica, 40-330 g column, ISCO, 0-40% EtOAc in pentane/cyclohexane) to afford the title compound.

(3-Fluorophenylamino)-acetic acid tert-butyl ester

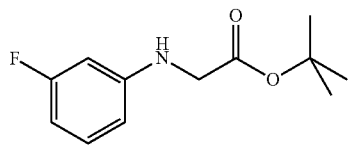 [SMILES: CC(C)(C)OC(=O)CNc1cccc(F)c1]

Following general method 1, employing 3-fluoroaniline, afforded the title compound as a yellow oil (19.3 g, 95%): $^1$H NMR (CDCl$_3$, 300 MHz); 7.10 (dt, J=6.7, 8.2 Hz, 1H), 6.42 (m, 1H), 6.36 (m, 1H), 6.27 (dt, J=11.4, 2.3 Hz, 1H), 4.4 (br. s, 1H), 3.77 (s, 2H), 1.49 (s, 9H).

(4-Trifluoromethylphenylamino)-acetic acid tert-butyl ester

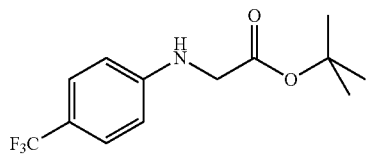 [SMILES: CC(C)(C)OC(=O)CNc1ccc(C(F)(F)F)cc1]

Following general method 1, employing 4-trifluoromethylaniline, afforded the title compound as an off-white solid (4.36 g, 53%); $^1$H NMR (CDCl$_3$, 300 MHz): 7.42 (d, J=8.5 Hz, 2H), 6.59 (d, J=8.5 Hz, 2H), 4.60 (br. s, 1H), 3.82 (d, J=5.2 Hz, 2H), 1.50 (s, 9H).

(4-Cyanophenylamino)-acetic acid tert-butyl ester

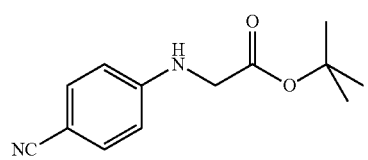 [SMILES: CC(C)(C)OC(=O)CNc1ccc(C#N)cc1]

Following general method 1, employing 4-cyanoaniline, afforded the title compound as an off-white solid (6.38 g, 67%); $^1$H NMR (CDCl$_3$, 300 MHz): 7.44 (d, J=8.7 Hz, 2H), 6.55 (d, J=8.8 Hz, 2H), 4.81 (br. s, 1H), 3.82 (d, J=5.0 Hz, 2H), 1.50 (s, 9H).

(4-Chloro-3-fluorophenylamino)-acetic acid tert-butyl ester

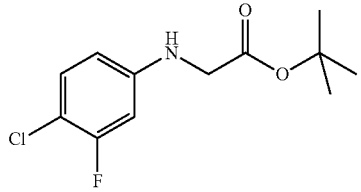 [SMILES: CC(C)(C)OC(=O)CNc1ccc(Cl)c(F)c1]

Following general method 1, employing 4-chloro-3-fluoroaniline, afforded the title compound as an off-white solid (4.76 g, 92%); $^1$H NMR (CDCl$_3$, 300 MHz): 7.17-7.09 (m, 1H), 6.38-6.28 (m, 2H), 4.45 (br. s, 1H), 3.75 (s, 2H), 1.49 (s, 8H).

(3-Fluoro-4-trifluoromethylphenylamino)-acetic acid tert-butyl ester

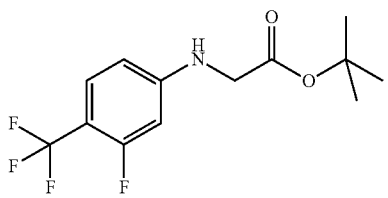 [SMILES: CC(C)(C)OC(=O)CNc1ccc(C(F)(F)F)c(F)c1]

Following general method 1, employing 4-amino-2-fluorobenzotrifluoride, afforded the title compound as an off-white solid (1.92 g, 44%); $^1$H NMR (CDCl$_3$, 300 MHz): 7.34 (t, J=8.4 Hz, 1H), 6.38-6.26 (m, 2H), 4.65 (br. s, 1H), 3.79 (s, 2H), 1.50 (s, 9H).

(3-Chloro-4-trifluoromethylphenylamino)-acetic acid tert-butyl ester

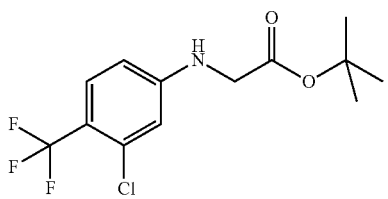 [SMILES: CC(C)(C)OC(=O)CNc1ccc(C(F)(F)F)c(Cl)c1]

Following general method 1, employing 4-amino-2-chlorobenzotrifluoride, afforded the title compound as an off-white solid (6.65 g, 84%); $^1$H NMR (CDCl$_3$, 300 MHz): 7.44 (d, J=8.7 Hz, 1H), 6.63 (d, J=2.4 Hz, 1H), 6.46 (dd, J=8.7, 2.3 Hz, 1H), 4.45 (br. s, 1H), 3.80 (s, 2H), 1.50 (s, 9H).

General Method 2: Preparation of 3-amino-1-(aryl)-1H-pyrrole-2,4-dicarboxylic acid 2-tert-butyl ester 4-ethyl esters To a solution of tert-butyl N-arylglycinate (3.8-85.8 mmol, 1 eq.) in toluene was added DBU (2.0-3.0 eq.) and ethyl (ethoxymethylene)cyanoacetate (2.0-3.0 eq.). The reaction mixture was stirred at 110-120° C., under nitrogen atmosphere, for 3-18 hours. The reaction mixture was then cooled, treated with saturated aqueous ammonium chloride solution and partitioned between EtOAc or DCM and water. The aqueous layer was further extracted with EtOAc or DCM. The combined organic layers were washed with saturated sodium bicarbonate solution, brine, dried and concentrated. The crude residue was then purified by flash chromatography (silica, 80-330 g column, ISCO, 0-40% EtOAc in pentane/hexane or 0-100% DCM in pentane) to afford the title compound.

3-Amino-1-(3-fluorophenyl)-1H-pyrrole-2,4-dicarboxylic acid 2-tert-butyl ester 4-ethyl ester

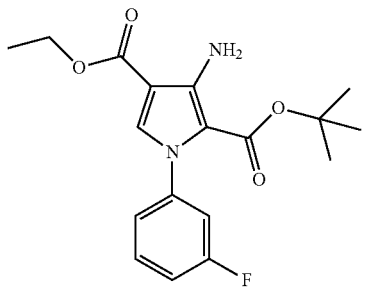 [SMILES: CCOC(=O)c1cn(-c2cccc(F)c2)c(C(=O)OC(C)(C)C)c1N]

Following general method 2, employing (3-fluorophenylamino)-acetic acid tert-butyl ester, afforded the title compound as a pale yellow solid (9.5 g, 32%); LCMS (method B): $R_T$=4.22 min, M+H$^+$=349; $^1$H NMR (CDCl$_3$, 300 MHz): 7.36 (dt, J=8.2, 6.2 Hz, 1H), 7.18 (s, 1H), 7.14-7.04 (m, 2H), 7.00 (dt, J=9.3, 2.2 Hz, 1H), 5.82 (s, 2H), 4.29 (q, J=7.1 Hz, 2H), 1.33 (t, J=7.1 Hz, 3H), 1.30 (s, 9H).

3-Amino-1-(4-trifluoromethylphenyl)-1H-pyrrole-2,4-dicarboxylic acid 2-tert-butyl ester 4-ethyl ester

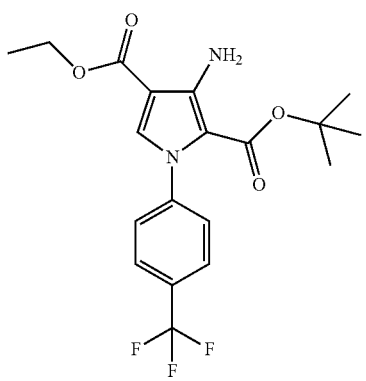 [SMILES: CCOC(=O)c1cn(-c2ccc(C(F)(F)F)cc2)c(C(=O)OC(C)(C)C)c1N]

Following general method 2, employing (4-trifluoromethylphenylamino)-acetic acid tert-butyl ester, afforded the title compound as an off-white solid (1.86 g, 41%); LCMS (method B): $R_T$=4.59 min, M+H$^+$=399; $^1$H NMR (CDCl$_3$, 400 MHz): 7.67 (d, J=8.3 Hz, 2H), 7.39 (d, J=8.2 Hz, 2H), 7.19 (s, 1H), 5.82 (br. s, 2H), 4.30 (q, J=7.1 Hz, 2H), 1.34 (t, J=7.1 Hz, 3H), 1.29 (s, 9H).

3-Amino-1-(4-cyanophenyl)-1H-pyrrole-2,4-dicarboxylic acid 2-tert-butyl ester 4-ethyl ester

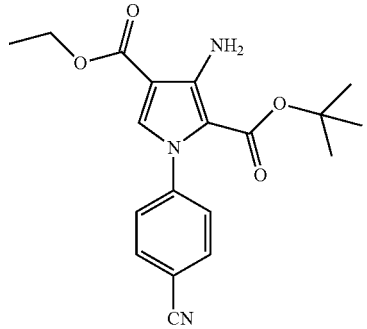 [SMILES: CCOC(=O)c1cn(-c2ccc(C#N)cc2)c(C(=O)OC(C)(C)C)c1N]

Following general method 2, employing (4-cyanophenylamino)-acetic acid tert-butyl ester, afforded the title compound as a white solid (6.26 g, 65%); LCMS (method B): $R_T$=3.98 min, M+H$^+$=356; $^1$H NMR (CDCl$_3$, 300 MHz): 7.71 (d, J=8.3 Hz, 2H), 7.38 (d, J=8.4 Hz, 2H), 7.21 (s, 1H), 5.84 (s, 2H), 4.30 (q, J=7.1 Hz, 2H), 1.37-1.31 (m, 12H).

3-Amino-1-(4-chloro-3-fluorophenyl)-1H-pyrrole-2,4-dicarboxylic acid 2-tert-butyl ester 4-ethyl ester

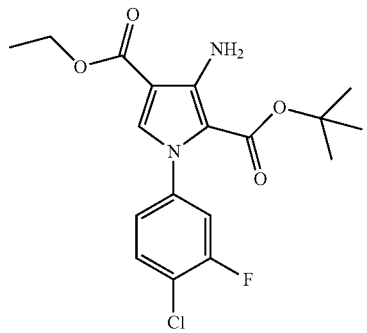 [SMILES: CCOC(=O)c1cn(-c2ccc(Cl)c(F)c2)c(C(=O)OC(C)(C)C)c1N]

Following general method 2, employing (4-chloro-3-fluorophenylamino)-acetic acid tert-butyl ester, afforded the title compound as a white solid (2.20 g, 31%); LCMS (method B): $R_T$=4.42 min, M+H$^+$=383; $^1$H NMR (CDCl$_3$, 300 MHz): 7.43 (t, J=8.2 Hz, 1H), 7.17 (s, 1H), 7.10 (dd, J=9.3, 2.4 Hz, 1H), 7.03 (ddd, J=8.5, 2.4, 1.2 Hz, 1H), 4.30 (q, J=7.1 Hz, 2H), 1.38-1.29 (m, 12H).

3-Amino-1-(3-fluoro-4-trifluoromethylphenyl)-1H-pyrrole-2,4-dicarboxylic acid 2-tert-butyl ester 4-ethyl ester

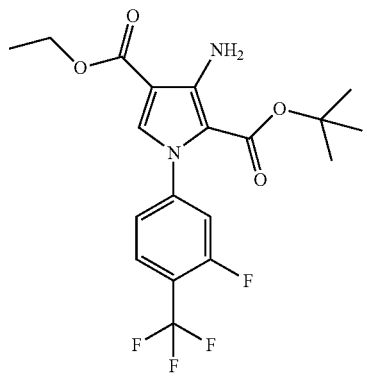 [SMILES: CCOC(=O)c1cn(-c2ccc(C(F)(F)F)c(F)c2)c(C(=O)OC(C)(C)C)c1N]

Following general method 2, employing (3-fluoro-4-trifluoromethylphenylamino) acetic acid tert-butyl ester, afforded the title compound as an off-white solid (1.68 g, 62%); LCMS (method B): $R_T$=4.43 min, M+H⁺=417; ¹H NMR (CDCl₃, 300 MHz): 7.65 (t, J=8.1 Hz, 1H), 7.22 (s, 1H), 7.21-7.13 (m, 2H), 4.31 (q, J=7.1 Hz, 2H), 1.39-1.30 (m, 12H).

3-Amino-1-(3-chloro-4-trifluoromethylphenyl)-1H-pyrrole-2,4-dicarboxylic acid 2-tert-butyl ester 4-ethyl ester

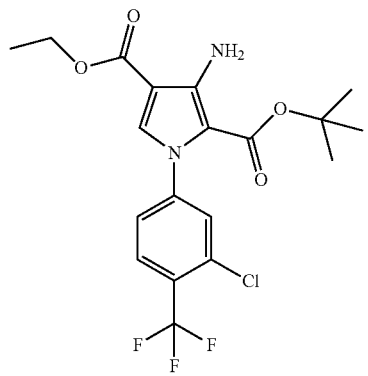 [SMILES: CCOC(=O)c1cn(-c2ccc(C(F)(F)F)c(Cl)c2)c(C(=O)OC(C)(C)C)c1N]

Following general method 2, employing (3-chloro-4-trifluoromethylphenylamino) acetic acid tert-butyl ester, afforded the title compound as a yellow solid (5.30 g, 57%); ¹H NMR (DMSO-D₆, 300 MHz): 7.93 (d, J=8.5 Hz, 1H), 7.83 (d, J=2.0 Hz, 1H), 7.64 (s, 1H), 7.57 (dd, J=8.4, 2.0 Hz, 1H), 5.96 (s, 2H), 4.23 (q, J=7.1 Hz, 2H), 1.27 (t, J=7.1 Hz, 3H), 1.23 (s, 9H).

General Method 3: Preparation of 1-(aryl)-4-ureido-1H-pyrrole-3-carboxylic acid ethyl esters To 3-amino-1-(aryl)-1H-pyrrole-2,4-dicarboxylic acid 2-tert-butyl ester 4-ethyl ester (0.15-4.63 mmol, 1.0 eq.), was added TFA (5.0-23 mL, 40 eq.). The reaction mixture was stirred at room temperature for 1-3 hours and was then evaporated to dryness. To the resultant residue was added dry THF, under nitrogen, followed by dropwise addition of trichloroacetyl isocyanate (1.1 eq.). The reaction mixture was stirred at room temperature for 1-3 hours and then evaporated to dryness. To the resultant residue was added 2 N ammonia in methanol (10 eq.), and the reaction mixture was stirred at room temperature for 2-16 hours. After this time, the solvent was removed in vacuo to yield the crude residue. Where purification was required the resultant residue was loaded onto H-MN and was then purified by flash chromatography (silica, 40-120 g column, ISCO, 0-100% EtOAc in DCM or 0-10% MeOH in DCM) to afford the title compound.

1-(3-Fluorophenyl)-4-ureido-1H-pyrrole-3-carboxylic acid ethyl ester

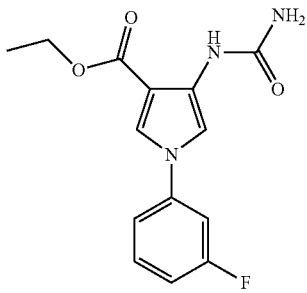 [SMILES: CCOC(=O)c1cn(-c2cccc(F)c2)cc1NC(N)=O]

Following general method 3, employing 3-amino-1-(3-fluorophenyl)-1H-pyrrole-2,4-dicarboxylic acid 2-tert-butyl ester 4-ethyl ester, afforded the title compound as an orange oil (0.99 g, 74%); LCMS (method B): $R_T$=3.21 min, M+H⁺=292; ¹H NMR (CDCl₃, 300 MHz): 8.50 (s, 1H), 7.62 (d, J=2.7 Hz, 1H), 7.46 (d, J=2.7 Hz, 1H), 7.40 (dt, J=8.2, 6.2 Hz, 1H), 7.23 (ddd, J=8.2, 2.2, 0.9 Hz, 1H), 7.16 (dt, J=9.8, 2.2 Hz, 1H), 6.99 (tdd, J=8.2, 2.2, 0.9 Hz, 1H), 4.76 (s, 2H), 4.31 (q, J=7.1 Hz, 2H), 1.37 (t, J=7.1 Hz, 3H).

1-(4-Trifluoromethylphenyl)-4-ureido-1H-pyrrole-3-carboxylic acid ethyl ester

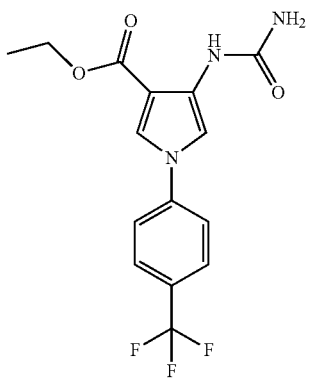 [SMILES: CCOC(=O)c1cn(-c2ccc(C(F)(F)F)cc2)cc1NC(N)=O]

Following general method 3, employing 3-amino-1-(3-fluorophenyl)-1H-pyrrole-2,4-dicarboxylic acid 2-tert-butyl ester 4-ethyl ester, afforded the title compound as an off-white solid (0.50 g, 58%); LCMS (method B): $R_T$=3.52 min, M+H⁺=342; ¹H NMR (DMSO-D₆, 400 MHz): 8.34 (s, 1H), 7.96 (d, J=2.8 Hz, 1H), 7.87 (d, J=8.7 Hz, 2H), 7.82 (d, J=8.7 Hz, 2H), 7.70 (d, J=2.7 Hz, 1H), 6.42 (br. s, 2H), 4.29 (q, J=7.1 Hz, 2H), 1.32 (t, J=7.1 Hz, 3H).

1-(4-Cyanophenyl)-4-ureido-1H-pyrrole-3-carboxylic acid ethyl ester

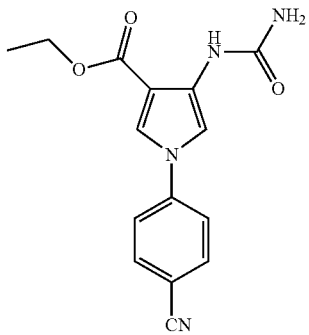 [SMILES: CCOC(=O)c1cn(-c2ccc(C#N)cc2)cc1NC(N)=O]

Following general method 3, employing 3-amino-1-(3-cyanophenyl)-1H-pyrrole-2,4-dicarboxylic acid 2-tert-butyl ester 4-ethyl ester, afforded the title compound as an off-white solid (0.226 g, 61%); LCMS (method B): $R_T$=3.02 min, M+H⁺=299; ¹H NMR (CDCl₃, 300 MHz): 8.49 (s, 1H), 7.76-7.71 (m, 2H), 7.69 (d, J=2.7 Hz, 1H), 7.58-7.52 (m, 3H), 4.66 (s, 2H), 4.33 (q, J=7.1 Hz, 2H), 1.38 (t, J=7.1 Hz, 3H).

1-(4-Chloro-3-fluorophenyl)-4-ureido-1H-pyrrole-3-carboxylic acid ethyl ester

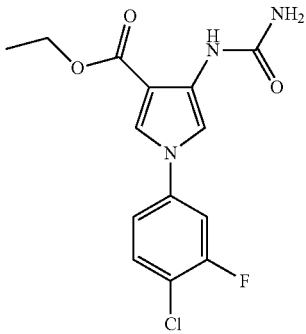 [SMILES: CCOC(=O)c1cn(-c2ccc(Cl)c(F)c2)cc1NC(N)=O]

Following general method 3, employing 3-amino-1-(4-chloro-3-fluorophenyl)-1H-pyrrole-2,4-dicarboxylic acid 2-tert-butyl ester 4-ethyl ester, afforded the title compound as an off-white solid (0.998 g, 100%); LCMS (method B): $R_T$=3.44 min, M+H$^+$=326; $^1$H NMR (DMSO-D$_6$, 300 MHz): 8.33 (s, 1H), 7.92 (d, J=2.7 Hz, 1H), 7.88 (dd, J=11.0, 2.6 Hz, 1H), 7.69-7.61 (m, 2H), 7.55-7.50 (m, 1H), 6.43 (s, 2H), 4.28 (q, J=7.1 Hz, 2H), 1.31 (t, J=7.1 Hz, 3H).

1-(3-Fluoro-4-trifluoromethylphenyl)-4-ureido-1H-pyrrole-3-carboxylic acid ethyl ester

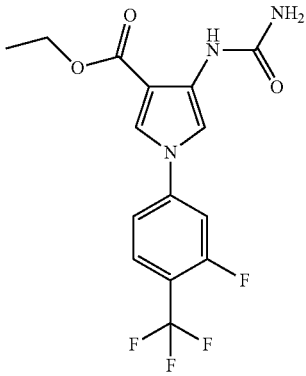 [SMILES: CCOC(=O)c1cn(-c2ccc(C(F)(F)F)c(F)c2)cc1NC(N)=O]

Following general method 3, employing 3-amino-1-(3-fluoro-4-trifluoromethyl phenyl)-1H-pyrrole-2,4-dicarboxylic acid 2-tert-butyl ester 4-ethyl ester, afforded the title compound as a yellow solid (1.38 g, 96%); LCMS (method B): $R_T$=3.53 min, M+H$^+$=360; $^1$H NMR (CDCl$_3$, 300 MHz): 8.49 (s, 1H), 7.71-7.64 (m, 2H), 7.51 (d, J=2.7 Hz, 1H), 7.35-7.27 (m, 2H), 4.67 (br. s, 2H), 4.33 (q, J=7.1 Hz, 2H), 1.38 (t, J=7.1 Hz, 3H).

1-(3-Chloro-4-trifluoromethylphenyl)-4-ureido-1H-pyrrole-3-carboxylic acid ethyl ester

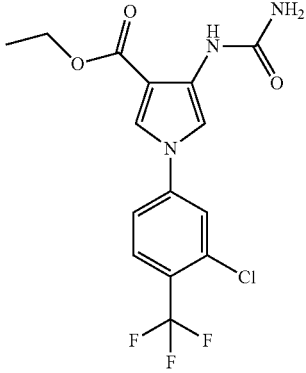 [SMILES: CCOC(=O)c1cn(-c2ccc(C(F)(F)F)c(Cl)c2)cc1NC(N)=O]

Following general method 3, employing 3-amino-1-(3-chloro-4-trifluoromethyl phenyl)-1H-pyrrole-2,4-dicarboxylic acid 2-tert-butyl ester 4-ethyl ester, afforded the title compound as a yellow solid (1.73 g, 100%); LCMS (method B): $R_T$=3.70 min, M+H$^+$=376; $^1$H NMR (DMSO-D$_6$, 300 MHz): 8.42 (s, 2H), 8.36 (s, 1H), 8.30 (s, 2H), 8.14 (d, J=2.2 Hz, 1H), 8.09 (d, J=2.3 Hz, 1H), 7.90 (d, J=8.8 Hz, 1H), 7.80 (dd, J=8.7, 2.2 Hz, 1H), 7.73 (d, J=2.8 Hz, 1H), 6.46 (s, 2H), 4.29 (q, J=7.1 Hz, 2H), 1.33 (t, J=7.1 Hz, 3H).

General Method 4: Preparation of 4-(3-alkyl-ureido)-1-(3-fluorophenyl)-1H-pyrrole-3-carboxylic acid ethyl esters To 3-amino-1-(aryl)-1H-pyrrole-2,4-dicarboxylic acid 2-tert-butyl ester 4-ethyl ester (0.82-0.86 mmol, 1.0 eq.), was added TFA (2.4-3.0 mL). The reaction mixture was stirred at room temperature for 1-3 hours and was then evaporated to dryness. To the resultant residue was added dry THF, under nitrogen, followed by dropwise addition of alkyl isocyanate (2.0 eq.). The reaction mixture was stirred at room temperature for 1-16 hours and then evaporated to dryness. The resulatant residue was dissolved in DCM and then filtered through a flash NH$_2$ cartridge, eluting further with MeOH. The combined organic washings were then loaded onto H-MN and concentrated in vacuo and purified by flash chromatography (silica, 40-120 g column, ISCO, 0-50% EtOAc in DCM or 0-30% EtOAc in pentane) or by (silica, 10-50 g Si-SPE column, Isolute, 50% DCM in pentane, DCM, then 20% MeOH in DCM) to afford the title compound.

1-(3-Fluorophenyl)-4-(3-methyl-ureido)-1H-pyrrole-3-carboxylic acid ethyl ester

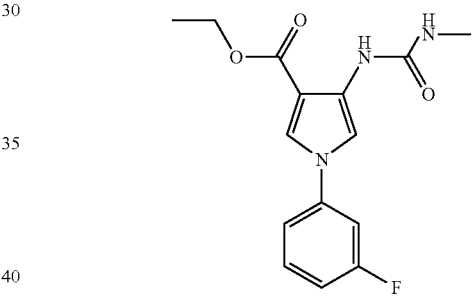

Following general method 4, employing 3-amino-1-(3-fluorophenyl)-1H-pyrrole-2,4-dicarboxylic acid 2-tert-butyl ester 4-ethyl ester and methyl isocyanate, afforded the title compound as a white solid (194 mg, 74%); LCMS (method B): $R_T$=3.38 min, M+H$^+$=306; $^1$H NMR (CDCl$_3$, 300 MHz): 8.42 (s, 1H), 7.64 (d, J=2.7 Hz, 1H), 7.46 (d, J=2.7 Hz, 1H), 7.39 (dt, J=8.2, 6.2 Hz, 1H), 7.24-7.20 (m, 1H), 7.15 (dt, J=9.9, 2.3 Hz, 1H), 6.99 (tdd, J=8.3, 2.4, 0.9 Hz, 1H), 4.71-4.65 (m, 1H), 4.31 (q, J=7.1 Hz, 2H), 2.90 (d, J=4.9 Hz, 3H), 1.37 (t, J=7.1 Hz, 3H).

4-(3-Ethyl-ureido)-1-(3-fluorophenyl)-1H-pyrrole-3-carboxylic acid ethyl ester

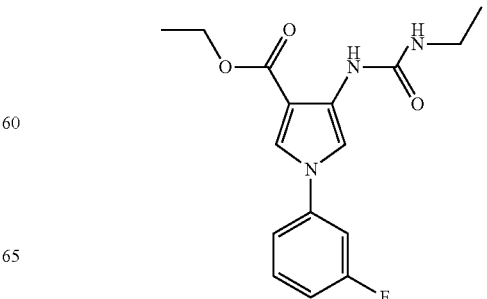

Following general method 4, employing 3-amino-1-(3-fluorophenyl)-1H-pyrrole-2,4-dicarboxylic acid 2-tert-butyl ester 4-ethyl ester and ethyl isocyanate, afforded the title compound as a cream solid (0.192 g, 73%); LCMS (method B): $R_T$=3.61 min, M+H$^+$=320; $^1$H NMR (CDCl$_3$, 300 MHz): 8.41 (s, 1H), 7.62 (d, J=2.7 Hz, 1H), 7.44 (d, J=2.7 Hz, 1H), 7.38 (dt, J=8.2, 6.2 Hz, 1H), 7.21 (dd, J=8.2, 2.4 Hz, 1H), 7.14 (dt, J=9.9, 2.4 Hz, 1H), 6.98 (td, J=8.2, 2.4 Hz, 1H), 4.73 (s, 1H), 4.31 (q, J=7.1 Hz, 2H), 3.35-3.26 (m, 2H), 1.37 (t, J=7.1 Hz, 3H), 1.21 (t, J=7.1 Hz, 3H).

1-(3-Fluorophenyl)-4-(3-isopropyl-ureido)-1H-pyrrole-3-carboxylic acid ethyl ester

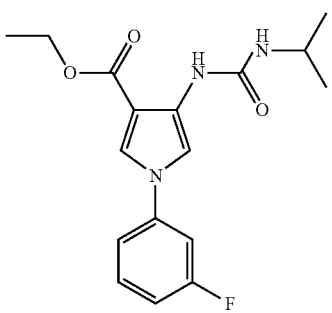 [SMILES: CCOC(=O)c1cn(-c2cccc(F)c2)cc1NC(=O)NC(C)C]

Following general method 4, employing 3-amino-1-(3-fluorophenyl)-1H-pyrrole-2,4-dicarboxylic acid 2-tert-butyl ester 4-ethyl ester and isopropyl isocyanate, afforded the title compound as an off-white solid (0.150 g, 55%); LCMS (method B): $R_T$=3.77 min, M+H$^+$=334; $^1$H NMR (CDCl$_3$, 300 MHz): 8.35 (s, 1H), 7.62 (d, J=2.7 Hz, 1H), 7.45 (d, J=2.7 Hz, 1H), 7.38 (dt, J=8.2, 6.2 Hz, 1H), 7.22 (ddd, J=8.2, 2.3, 0.9 Hz, 1H), 7.15 (dt, J=9.9, 2.3 Hz, 1H), 6.98 (tdd, J=8.2, 2.3, 0.9 Hz, 1H), 4.52 (br. s, 1H), 4.31 (q, J=7.1 Hz, 2H), 3.94 (br. s, 1H), 1.37 (t, J=7.1 Hz, 3H), 1.22 (d, J=6.5 Hz, 6H).

1-(4-Chloro-3-fluoro-phenyl)-4-(3-ethyl-ureido)-1H-pyrrole-3-carboxylic acid ethyl ester

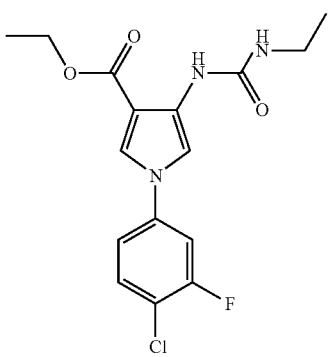 [SMILES: CCNC(=O)Nc1cn(-c2ccc(Cl)c(F)c2)cc1C(=O)OCC]

Following general method 4, employing 3-amino-1-(4-chloro-3-fluoro-phenyl)-1H-pyrrole-2,4-dicarboxylic acid 2-tert-butyl ester 4-ethyl ester and ethyl isocyanate, afforded the title compound as a yellow solid (0.65 g, 76%); LCMS (method B): $R_T$=3.87 min, M+H$^+$=354; $^1$H NMR (DMSO-D$_6$, 400 MHz): 8.27 (s, 1H), 7.91 (d, J=2.7 Hz, 1H), 7.86 (dd, J=10.9, 2.6 Hz, 1H), 7.68-7.63 (m, 2H), 7.54-7.50 (m, 1H), 7.23 (t, J=5.3 Hz, 1H), 4.28 (q, J=7.1 Hz, 2H), 3.13-3.05 (m, 2H), 1.31 (t, J=7.1 Hz, 3H), 1.05 (t, J=7.2 Hz, 3H).

General Method 5: Preparation of (S)-3-{[1-(3-aryl)-4-ureido-1H-pyrrole-3-carbonyl]-amino}-piperidine-1-carboxylic acid tert-butyl esters To a solution of (S)-3-amino-1-Boc-piperidine (0.8-1.5 eq.) in THF, under nitrogen, was added 2N trimethylaluminium in hexanes (2.0-3.3 eq.), and the reaction mixture was allowed to stir at room temperature for 0.25-2 hours. After this time, a THF solution of 1-(aryl)-4-ureido-1H-pyrrole-3-carboxylic acid ethyl ester (0.59-3.26 mmol, 1.0 eq.), was added and the reaction mixture was heated at 65-70° C. for a period of 3.5-24 hours. After this time, the reaction mixture was allowed to cool and was then quenched by addition of a saturated solution of Rochelle's salt. After 0.25-0.5 hours, the mixture was extracted with EtOAc or DCM and the organic layer was washed with water, brine, dried and concentrated. The resultant residue was then purified by flash chromatography (silica, 12-120 g column, ISCO, 0-100% EtOAc in DCM) to afford the title compound.

(S)-3-{[1-(3-Fluorophenyl)-4-ureido-1H-pyrrole-3-carbonyl]-amino}-piperidine-1-carboxylic acid tert-butyl ester

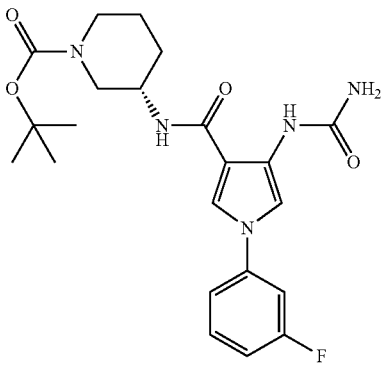 [SMILES: CC(C)(C)OC(=O)N1CCC[C@H](NC(=O)c2cn(-c3cccc(F)c3)cc2NC(N)=O)C1]

Following general method 5, employing 1-(3-fluorophenyl)-4-ureido-1H-pyrrole-3-carboxylic acid ethyl ester, afforded the title compound as an orange solid (0.51 g, 35%); LCMS (method B): $R_T$=3.38 min, M+H$^+$=446; $^1$H NMR (CDCl$_3$, 300 MHz): 9.15 (s, 1H), 7.61 (d, J=2.5 Hz, 1H), 7.35 (dt, J=8.2, 6.2 Hz, 1H), 7.25 (br. s, 1H), 7.15 (ddd, J=8.2, 2.2, 0.9 Hz, 1H), 7.07 (dt, J=9.9, 2.2 Hz, 1H), 6.95 (tdd, J=8.2, 2.5, 0.9 Hz, 1H), 6.36 (br. s, 1H), 4.92 (s, 2H), 4.02 (m, 1H), 3.62 (dd, J=13.3, 3.5 Hz, 1H), 3.49-3.33 (m, 3H), 1.93-1.52 (m, 4H), 1.46 (s, 9H).

(S)-3-{[1-(4-Trifluoromethylphenyl)-ureido-1H-pyrrole-3-carbonyl]-amino}-piperidine-1-carboxylic acid tert-butyl ester

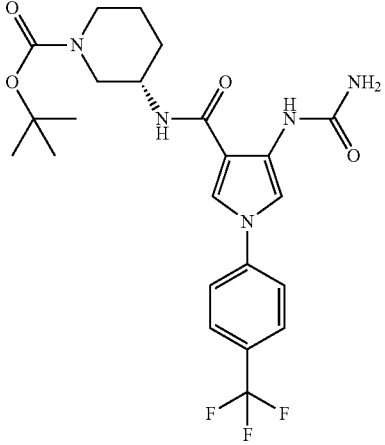 [SMILES: CC(C)(C)OC(=O)N1CCC[C@H](NC(=O)c2cn(-c3ccc(C(F)(F)F)cc3)cc2NC(N)=O)C1]

Following general method 5, employing 1-(4-trifluoromethylphenyl)-4-ureido-1H-pyrrole-3-carboxylic acid ethyl ester, afforded the title compound as an off-white solid (0.08 g, 40%); LCMS (method B): $R_T$=3.65 min, M+H$^+$=496; $^1$H NMR (CDCl$_3$, 400 MHz): 9.15 (s, 1H), 7.70-7.64 (m, 3H), 7.48 (d, J=8.4 Hz, 2H), 7.29-7.25 (m, 1H), 4.74 (s, 2H), 4.09-4.02 (m, 1H), 3.58-3.49 (m, 3H), 3.38-3.26 (m, 1H), 1.89-1.82 (m, 2H), 1.79-1.66 (m, 1H), 1.64-1.52 (m, 1H), 1.47 (s, 9H).

(S)-3-{[1-(4-Cyanophenyl)-4-ureido-1H-pyrrole-3-carbonyl]-amino}-piperidine-1-carboxylic acid tert-butyl ester

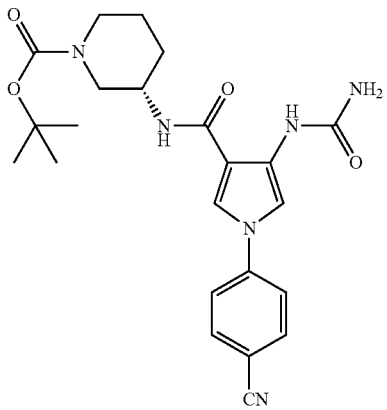 [SMILES: CC(C)(C)OC(=O)N1CCC[C@H](NC(=O)c2cn(-c3ccc(C#N)cc3)cc2NC(N)=O)C1]

Following general method 5, employing 1-(4-cyanophenyl)-4-ureido-1H-pyrrole-3-carboxylic acid ethyl ester, afforded the title compound as an off-white solid (0.105 g, 23%); LCMS (method B): $R_T$=3.16 min, M+H$^+$=453; $^1$H NMR (CDCl$_3$, 300 MHz): 9.17 (s, 1H), 7.73-7.63 (m, 3H), 7.44 (d, J=8.3 Hz, 2H), 7.34-7.30 (m, 1H), 6.47 (br. s, 1H), 4.97 (s, 2H), 4.09-3.96 (m, 1H), 3.51-3.32 (m, 3H), 1.95-1.64 (m, 3H), 1.64-1.50 (m, 1H), 1.46 (s, 9H).

(S)-3-{[1-(4-Chloro-3-fluorophenyl)-4-ureido-1H-pyrrole-3-carbonyl]-amino}-piperidine-1-carboxylic acid tert-butyl ester

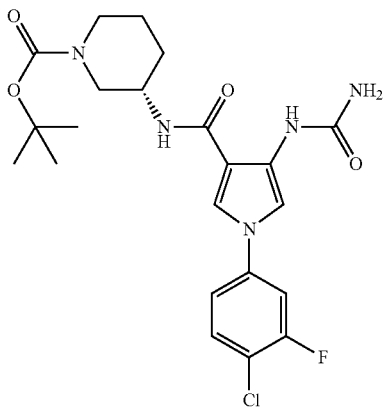 [SMILES: CC(C)(C)OC(=O)N1CCC[C@H](NC(=O)c2cn(-c3ccc(Cl)c(F)c3)cc2NC(N)=O)C1]

Following general method 5, employing 1-(4-chloro-3-fluorophenyl)-4-ureido-1H-pyrrole-3-carboxylic acid ethyl ester, afforded the title compound as a pale yellow glass (212 mg, 25%): LCMS (method B); $R_T$=3.57 min, M+H$^+$=480; $^1$H NMR (CDCl$_3$, 300 MHz): 9.15 (s, 1H), 7.55 (d, J=2.5 Hz, 1H), 7.39 (t, J=8.3 Hz, 1H), 7.34-7.22 (m, 1H), 7.15 (dd, J=9.9, 2.6 Hz, 1H), 7.11-7.05 (m, 1H), 6.50 (br. s, 1H), 5.07 (s, 2H), 4.07-3.94 (m, 1H), 3.72-3.58 (m, 1H), 3.48-3.27 (m, 3H), 1.95-1.82 (m, 1H), 1.81-1.63 (m, 2H), 1.62-1.50 (s, 1H), 1.46 (s, 9H).

(S)-3-{[1-(3-Fluoro-4-trifluoromethylphenyl)-4-ureido-1H-pyrrole-3-carbonyl]-amino}-piperidine-1-carboxylic acid tert-butyl ester

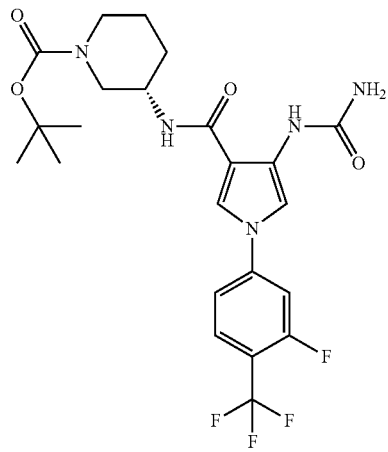 [SMILES: CC(C)(C)OC(=O)N1CCC[C@H](NC(=O)c2cn(-c3ccc(C(F)(F)F)c(F)c3)cc2NC(N)=O)C1]

Following general method 5, employing 1-(3-fluoro-4-trifluoromethylphenyl)-4-ureido-1H-pyrrole-3-carboxylic acid ethyl ester, afforded the title compound as a pale yellow glass (117 mg, 13%); LCMS (method B): $R_T$=3.67 min, M+H$^+$=514; $^1$H NMR (CDCl$_3$, 300 MHz): 9.16 (s, 1H), 7.67-7.55 (m, 2H), 7.40-7.30 (m, 1H), 7.27-7.14 (m, 2H), 6.53 (s, 1H), 5.03 (s, 2H), 4.08-3.96 (m, 1H), 3.70-3.57 (m, 1H), 3.49-3.32 (m, 3H), 1.92-1.64 (m, 3H), 1.63-1.52 (m, 1H), 1.47 (s, 9H).

(S)-3-{[1-(3-Chloro-4-trifluoromethylphenyl)-4-ureido-1H-pyrrole-3-carbonyl]-amino}-piperidine-1-carboxylic acid tert-butyl ester

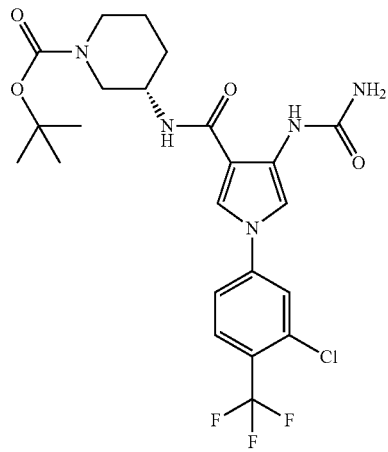 [SMILES: CC(C)(C)OC(=O)N1CCC[C@H](NC(=O)c2cn(-c3ccc(C(F)(F)F)c(Cl)c3)cc2NC(N)=O)C1]

Following general method 5, employing 1-(3-chloro-4-trifluoromethylphenyl)-4-ureido-1H-pyrrole-3-carboxylic acid ethyl ester, afforded the title compound as a off-white solid (220 mg, 31%); LCMS (method B): $R_T$=3.80 min, M+H$^+$=530.

(S)-3-{[1-(3-Fluorophenyl)-4-(3-methyl-ureido)-1H-pyrrole-3-carbonyl]-amino}-piperidine-1-carboxylic acid tert-butyl ester

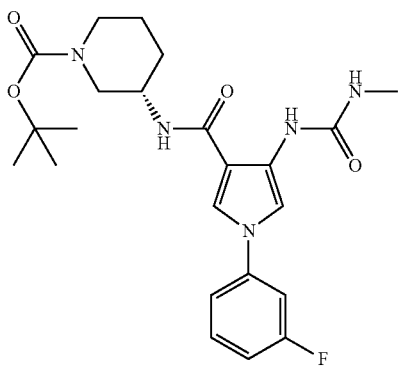 [SMILES: CNC(=O)Nc1cn(-c2cccc(F)c2)cc1C(=O)N[C@H]1CCCN(C(=O)OC(C)(C)C)C1]

Following general method 5, employing 1-(3-fluorophenyl)-4-(3-methyl-ureido)-1H-pyrrole-3-carboxylic acid ethyl ester, afforded the title compound as a glass (171 mg, 27%); LCMS (method B): $R_T$=3.54 min, M+H$^+$=460; $^1$H NMR (CDCl$_3$, 300 MHz): 8.42 (s, 1H), 7.64 (d, J=2.7 Hz, 1H), 7.46 (d, J=2.7 Hz, 1H), 7.39 (dt, J=8.2, 6.2 Hz, 1H), 7.24-7.20 (m, 1H), 7.15 (dt, J=9.9, 2.3 Hz, 1H), 6.99 (tdd, J=8.3, 2.4, 0.9 Hz, 1H), 4.71-4.65 (m, 1H), 4.31 (q, J=7.1 Hz, 2H), 2.90 (d, J=4.9 Hz, 3H), 1.37 (t, J=7.1 Hz, 3H).

(S)-3-{[4-(3-Ethyl-ureido)-1-(3-fluorophenyl)-1H-pyrrole-3-carbonyl]-amino}-piperidine-1-carboxylic acid tert-butyl ester

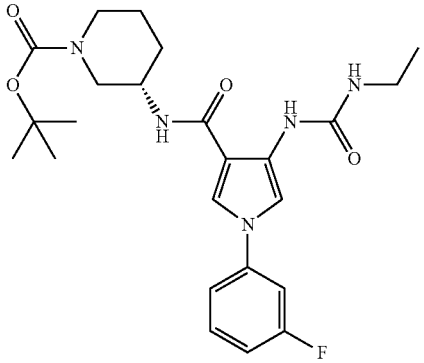 [SMILES: CCNC(=O)Nc1cn(-c2cccc(F)c2)cc1C(=O)N[C@H]1CCCN(C(=O)OC(C)(C)C)C1]

Following general method 5, employing 4-(3-ethyl-ureido)-1-(3-fluorophenyl)-1H-pyrrole-3-carboxylic acid ethyl ester, afforded the title compound as an off-white glass (257 mg, 46%); LCMS (method B): $R_T$=3.69 min, M+H$^+$=474; $^1$H NMR (CDCl$_3$, 300 MHz): 9.03 (s, 1H), 7.65 (d, J=2.4 Hz, 1H), 7.36 (dt, J=8.2, 6.2 Hz, 1H), 7.21-7.15 (m, 2H), 7.11 (dt, J=9.9, 2.4 Hz, 1H), 6.97 (ddt, J=8.2, 2.4, 0.7 Hz, 1H), 4.55 (m, 1H), 4.07 (m, 1H), 3.65-3.41 (m, 3H), 3.36-3.26 (m, 2H), 1.94-1.80 (m, 2H), 1.77-1.65 (m, 2H), 1.47 (s, 9H), 1.19 (t, 3H).

(S)-3-{[1-(3-Fluorophenyl)-4-(3-isopropyl-ureido)-1H-pyrrole-3-carbonyl]-amino-piperidine-1-carboxylic acid tert-butyl ester

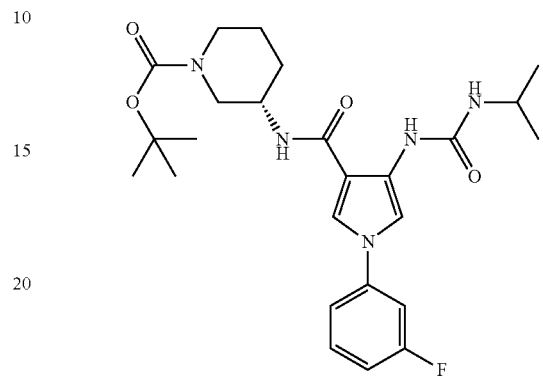

Following general method 5, employing 1-(3-fluorophenyl)-4-(3-isopropyl-ureido)-1H-pyrrole-3-carboxylic acid ethyl ester, afforded the title compound as a yellow solid (78 mg, 59%); LCMS (method B): $R_T$=3.88 min, M+H$^+$=488; $^1$H NMR (CDCl$_3$, 300 MHz): 8.99 (s, 1H), 7.64 (s, 1H), 7.37 (q, J=7.6 Hz, 1H), 7.21-7.15 (m, 2H), 7.11 (dd, J=10.0, 2.4 Hz, 1H), 6.96 (t, J=8.4 Hz, 1H), 6.20 (br. s, 1H), 4.46 (d, J=7.6 Hz, 1H), 4.07 (m, 1H), 3.94 (m, 1H), 3.65-3.43 (m, 3H), 3.32 (s, 1H), 1.93-1.80 (m, 2H), 1.73 (m, 1H), 1.58 (m, 1H), 1.47 (s, 9H), 1.21 (d, J=6.5 Hz, 6H).

(S)-3-{[1-(4-Chloro-3-fluoro-phenyl)-4-(3-ethyl-ureido)-1H-pyrrole-3-carbonyl]-amino}-piperidine-1-carboxylic acid tert-butyl ester

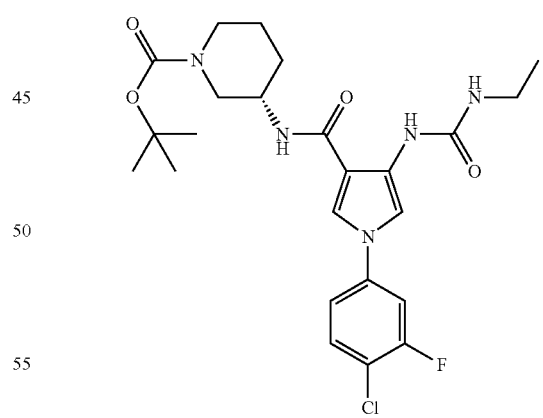

Following general method 5, employing 1-(4-chloro-3-fluoro-phenyl)-4-(3-ethyl-ureido)-1H-pyrrole-3-carboxylic acid ethyl ester afforded the title compound as a yellow foam (220 mg, 42%); LCMS (method B): $R_T$=3.94 min, M+H$^+$=508.

General Method 6: Preparation of (S)-3-{[1-(3-fluorophenyl)-4-(3-substituted-ureido)-1H-pyrrole-3-carbonyl]-amino-piperidine-1-carboxylic acid tert-butyl esters with conventional heating To a solution of (S)-3-{[1-(3-fluorophenyl)-4-ureido-1H-pyrrole-3-carbonyl]-amino}-piperidine-1-carboxylic acid tert-butyl ester (90-100 mg, 0.20-0.23 mmol, 1.0 eq.) and amine (1.0 eq.), in toluene, under nitrogen, was added acetic acid (0.8 eq.) and the reaction mixture was heated at 110° C. for 24-72 hours. After this time, the reaction mixture was allowed to cool and was partitioned between DCM and water. The DCM layer was passed through a hydrophobic frit and was then evaporated to yield the title compound as a crude residue.

General Method 7: Preparation of (S)-3-{[1-(3-fluorophenyl)-4-(3-substituted-ureido)-1H-pyrrole-3-carbonyl]-amino-piperidine-1-carboxylic acid tert-butyl esters with microwave irradiation.

To a solution of (S)-3-{[1-(3-fluorophenyl)-4-ureido-1H-pyrrole-3-carbonyl]-amino}-piperidine-1-carboxylic acid tert-butyl ester (75-100 mg, 0.17-0.23 mmol, 1.0 eq.) and amine (1.5 eq.), in toluene, under nitrogen, was added acetic acid (0.8 eq.) and the reaction mixture was heated under microwave irradiation at 150° C. for 1 hour. The reaction mixture was allowed to cool and was partitioned between DCM and water. The DCM layer was passed through a hydrophobic frit and was then evaporated to yield the title compound as a crude residue.

(S)-3-{[4-(3-Cyclopropylmethyl-ureido)-1-(3-fluorophenyl)-1H-pyrrole-3-carbonyl]-amino}-piperidine-1-carboxylic acid tert-butyl ester

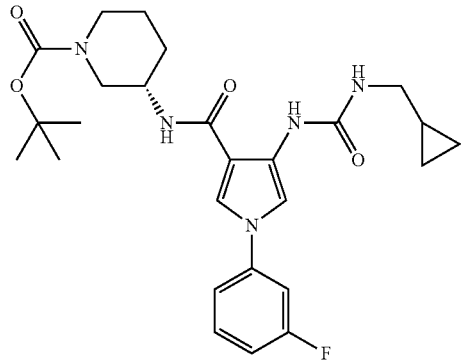 [SMILES: CC(C)(C)OC(=O)N1CCC[C@H](NC(=O)c2cn(-c3cccc(F)c3)cc2NC(=O)NCC2CC2)C1]

Following general method 6, employing (S)-3-{[1-(3-fluorophenyl)-4-ureido-1H-pyrrole-3-carbonyl]-amino}-piperidine-1-carboxylic acid tert-butyl ester and cyclopropanemethylamine, afforded the crude title compound as an orange foam (114 mg); LCMS (method B): $R_T$=3.94 min, M+H$^+$=500. This crude material was used in the next step without further purification.

(S)-3-({1-(3-Fluorophenyl)-4-[3-(2-methoxy-ethyl)-ureido]-1H-pyrrole-3-carbonyl}-amino)-piperidine-1-carboxylic acid tert-butyl ester

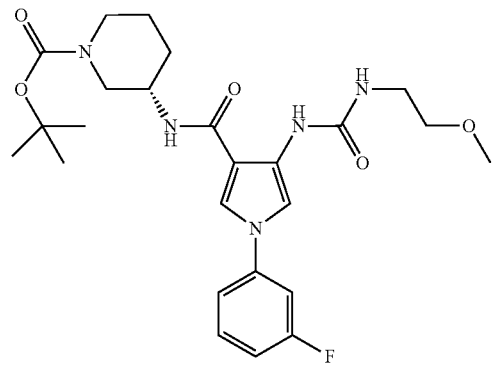 [SMILES: COCCNC(=O)Nc1cn(-c2cccc(F)c2)cc1C(=O)N[C@H]1CCCN(C(=O)OC(C)(C)C)C1]

Following general method 6, employing (S)-3-{[1-(3-fluorophenyl)-4-ureido-1H-pyrrole-3-carbonyl]-amino}-piperidine-1-carboxylic acid tert-butyl ester and 2-methoxyethylamine, afforded the crude title compound as an orange foam (109 mg); LCMS (method B): $R_T$=3.69 min, M+H$^+$=504. This crude material was used in the next step without further purification.

(S)-3-{[4-(3-Cyclopropylureido)-1-(3-fluoro-phenyl)-1H-pyrrole-3-carbonyl]-amino}-piperidine-1-carboxylic acid tert-butyl ester

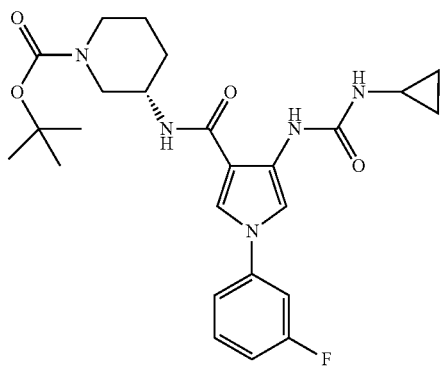 [SMILES: CC(C)(C)OC(=O)N1CCC[C@H](NC(=O)c2cn(-c3cccc(F)c3)cc2NC(=O)NC2CC2)C1]

Following general method 7, employing (S)-3-{[1-(3-fluorophenyl)-4-ureido-1H-pyrrole-3-carbonyl]-amino}-piperidine-1-carboxylic acid tert-butyl ester and cyclopropylamine, afforded the crude desired product. Column chromatography (silica, 12 g column, ISCO, 0-50% ethyl acetate in DCM) afforded the title compound as a glass (64 mg, 78%); LCMS (method B): $R_T$=3.70 min, M+H$^+$=486.

(S)-3-({1-(3-Fluorophenyl)-4-[3-(2-hydroxy-ethyl)-ureido]-1H-pyrrole-3-carbonyl}-amino)-piperidine-1-carboxylic acid tert-butyl ester

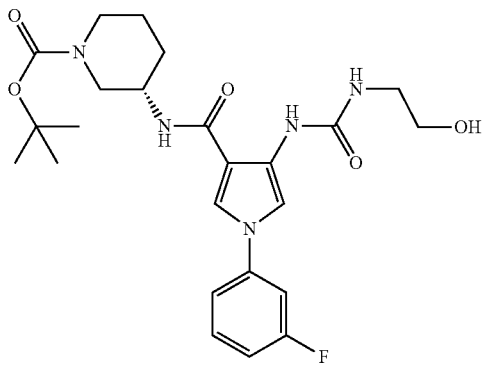 [SMILES: CC(C)(C)OC(=O)N1CCC[C@H](NC(=O)c2cn(-c3cccc(F)c3)cc2NC(=O)NCCO)C1]

Following general method 6, employing (S)-3-{[1-(3-fluorophenyl)-4-ureido-1H-pyrrole-3-carbonyl]-amino}-piperidine-1-carboxylic acid tert-butyl ester and 2-amino-ethanol, afforded the crude desired product. Column chromatography (silica, 12 g column, ISCO, 0-100% ethyl acetate in DCM) afforded the title compound as a glass (60 mg, 55%); LCMS (method B): $R_T$=3.25 min, M+H$^+$=490.

1-(3-Fluorophenyl)-4-(3-propyl-ureido)-1H-pyrrole-3-carboxylic acid (S)-piperidin-3-ylamide

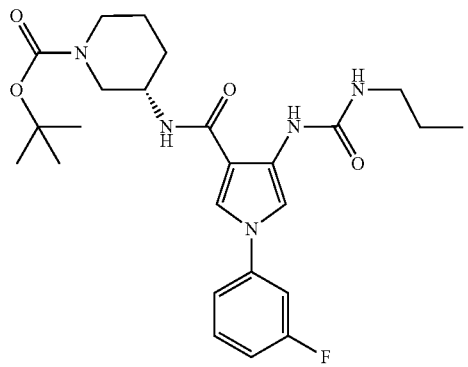 [SMILES: CCCNC(=O)Nc1cn(-c2cccc(F)c2)cc1C(=O)N[C@H]1CCCN(C(=O)OC(C)(C)C)C1]

Following general method 6, employing (S)-3-{[1-(3-fluorophenyl)-4-ureido-1H-pyrrole-3-carbonyl]-amino}-piperidine-1-carboxylic acid tert-butyl ester and propylamine, afforded the crude desired product. Column chromatography (silica, 12 g column, ISCO, 0-50% ethyl acetate in DCM) afforded the title compound as glass (100 mg, 65%); LCMS (method B): $R_T$=3.89 min, M+H$^+$=488.

(S)-3-({1-(3-Fluorophenyl)-4-[3-(3-hydroxy-propyl)-ureido]-1H-pyrrole-3-carbonyl}-amino)-piperidine-1-carboxylic acid tert-butyl ester

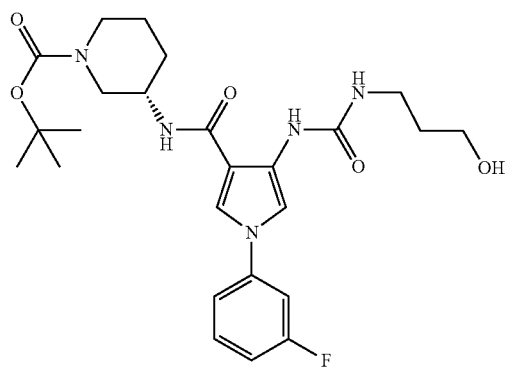 [SMILES: CC(C)(C)OC(=O)N1CCC[C@H](NC(=O)c2cn(-c3cccc(F)c3)cc2NC(=O)NCCCO)C1]

Following general method 6, employing (S)-3-{[1-(3-fluorophenyl)-4-ureido-1H-pyrrole-3-carbonyl]amino}-piperidine-1-carboxylic acid tert-butyl ester and 3-amino-propan-1-ol, afforded the crude desired product. Column chromatography (silica, 12 g column, ISCO, 0-100% ethyl acetate in DCM) afforded the title compound as a glass (70 mg, 60%); LCMS (method B): $R_T$=3.37 min, M+H$^+$=504.

(S)-3-({1-(3-Fluorophenyl)-4-[3-(3-methoxy-propyl)-ureido]-1H-pyrrole-3-carbonyl}-amino)-piperidine-1-carboxylic acid tert-butyl ester

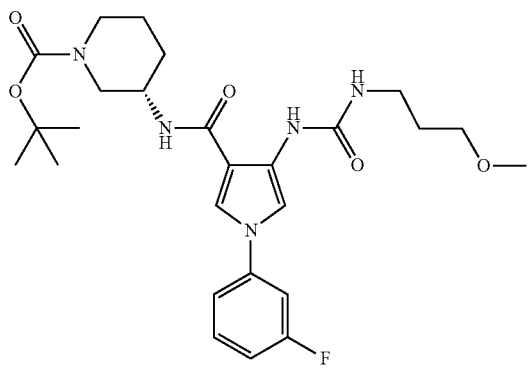 [SMILES: COCCCNC(=O)Nc1cn(-c2cccc(F)c2)cc1C(=O)N[C@H]1CCCN(C(=O)OC(C)(C)C)C1]

Following general method 6, employing (S)-3-{[1-(3-fluorophenyl)-4-ureido-1H-pyrrole-3-carbonyl]-amino}-piperidine-1-carboxylic acid tert-butyl ester and 3-methoxy-propylamine afforded the crude desired product. Column chromatography (silica, 12 g column, ISCO, 0-60% ethyl acetate in DCM) afforded the title compound as a glass (100 mg, 71%). LCMS (method B): $R_T$=3.67 min, M+H$^+$=518.

(S)-3-{[4-[3-(2-Fluoroethyl)-ureido]-1-(3-fluorophenyl)-1H-pyrrole-3-carbonyl]-amino}-piperidine-1-carboxylic acid tert-butyl ester

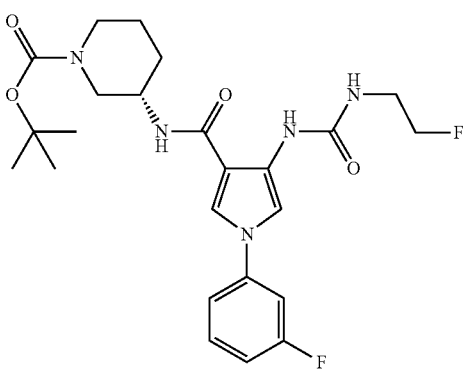 [SMILES: CC(C)(C)OC(=O)N1CCC[C@H](NC(=O)c2cn(-c3cccc(F)c3)cc2NC(=O)NCCF)C1]

Following general method 7, employing (S)-3-{[1-(3-fluorophenyl)-4-ureido-1H-pyrrole-3-carbonyl]-amino}-piperidine-1-carboxylic acid tert-butyl ester and 2-fluoroethylamine hydrochloride, afforded the crude desired product (Note: 0.34 mmol of anhydrous sodium acetate was added to the reaction mixture to neutralise the amine). Column chromatography (silica, 12 g column, ISCO, 0-100% ethyl acetate in DCM) afforded the title compound as a glass (80 mg, 95%). LCMS (method B): $R_T$=3.68 min, M+H$^+$=492.

(S)-3-{[4-[3-(2,2-Difluoroethyl)-ureido]-1-(3-fluorophenyl)-1H-pyrrole-3-carbonyl]-amino}-piperidine-1-carboxylic acid tert-butyl ester

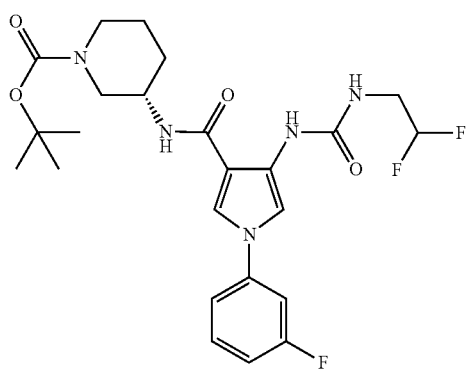 [SMILES: CC(C)(C)OC(=O)N1CCC[C@H](NC(=O)c2cn(-c3cccc(F)c3)cc2NC(=O)NCC(F)F)C1]

Following general method 7, employing (S)-3-{[1-(3-fluorophenyl)-4-ureido-1H-pyrrole-3-carbonyl]-amino}-piperidine-1-carboxylic acid tert-butyl ester and 2,2-difluoroethylamine, afforded the crude desired product. Column chromatography (silica, 12 g column, ISCO, 0-50% ethyl acetate in DCM) afforded the title compound as a glass (100 mg, 57%). LCMS (method B): $R_T$=3.81 min, M+H$^+$=510.

(S)-3-({1-(3-Fluorophenyl)-4-[3-(2,2,2-trifluoroethyl)-ureido]-1H-pyrrole-3-carbonyl}-amino)-piperidine-1-carboxylic acid tert-butyl ester

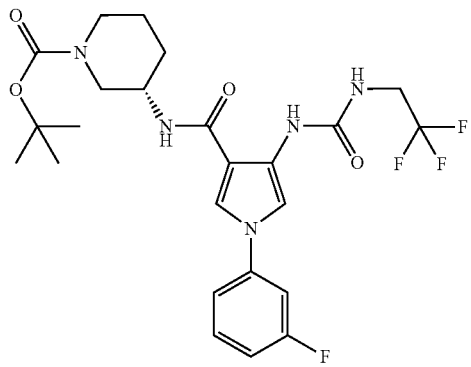 [SMILES: CC(C)(C)OC(=O)N1CCC[C@H](NC(=O)c2cn(-c3cccc(F)c3)cc2NC(=O)NCC(F)(F)F)C1]

Following general method 7, employing (S)-3-{[1-(3-fluorophenyl)-4-ureido-1H-pyrrole-3-carbonyl]-amino}-piperidine-1-carboxylic acid tert-butyl ester and 2,2,2-trifluoroethylamine, afforded the crude desired product. Column chromatography (silica, 12 g column, ISCO, 0-100% ethyl acetate in DCM) afforded the title compound as a glass (70 mg, 39%). LCMS (method B): $R_T$=4.00 min, M+H$^+$=528.

General Method 8: Preparation of 1-(aryl)-4-ureido-1H-pyrrole-3-carboxylic acid (S)-piperidin-3-ylamide To the (S)-3-{[1-(3-aryl)-4-ureido-1H-pyrrole-3-carbonyl]-amino}-piperidine-1-carboxylic acid tert-butyl ester (0.07-1.14 mmol, 1.0 eq.), was added TFA (0.2-3.4 mL, 40 eq.). The reaction mixture was stirred at room temperature for 1-3 hours and was then evaporated to dryness. The resultant crude residue was purified using one of the following methods to afford the title compound.

A=The crude residue was loaded onto H-MN and was then purified by flash chromatography (silica, 12-40 g column, ISCO, 0-30% MeOH in DCM);

B=Reverse phase HPLC (Phenomenex Gemini C18, 20 mM triethylamine in water on a 5-95% MeCN gradient);

C=Loaded onto an Isolute® SCX-2 cartridge with MeOH, washing the cartridge with MeOH, before eluting the desired product with 2N ammonia in MeOH.

D=Dissolved in DCM and filtered through a 5 g Isolute® flash NH2 cartridge, washing the cartridge with 10% MeOH in DCM, then 20% MeOH in DCM, then with MeOH, concentrating the filtrate in vacuo and subjecting the residue to purification by flash chromatography (silica, 12-40 g column, ISCO, 0-30% MeOH in DCM).

E=Trituration with acetonitrile

Example 1

1-(3-Fluorophenyl)-4-ureido-1H-pyrrole-3-carboxylic acid (S)-piperidin-3-ylamide

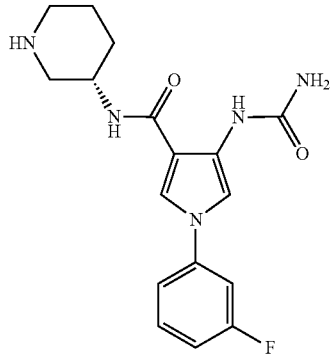 [SMILES: NC(=O)Nc1cn(-c2cccc(F)c2)cc1C(=O)N[C@H]1CCCNC1]

Following general method 8, employing (S)-3-{[1-(3-fluorophenyl)-4-ureido-1H-pyrrole-3-carbonyl]-amino}-piperidine-1-carboxylic acid tert-butyl ester, and purification method B, afforded the title compound as a cream solid (237 mg, 60%); LCMS (method A), $R_T$=5.18 min, M+H$^+$=346; $^1$H NMR (CD$_3$OD, 300 MHz): 7.80 (d, J=2.6 Hz, 1H), 7.53-7.44 (m, 2H), 7.33-7.24 (m, 2H), 7.04 (m, 1H), 3.98 (m, 1H), 3.16 (m, 1H), 2.93 (m, 1H), 2.59-2.49 (m, 2H), 1.98 (m, 1H), 1.79 (m, 1H), 1.61-1.51 (m, 2H).

Example 2

1-(4-Trifluoromethylphenyl)-4-ureido-1H-pyrrole-3-carboxylic acid (S)-piperidin-3-ylamide—TFA

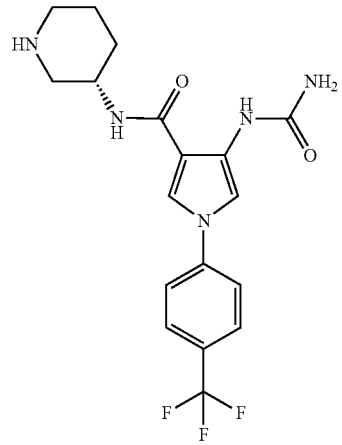 [SMILES: NC(=O)Nc1cn(-c2ccc(C(F)(F)F)cc2)cc1C(=O)N[C@H]1CCCNC1]

Following general method 8, employing (S)-3-{[1-(4-trifluoromethylphenyl)-4-ureido-1H-pyrrole-3-carbonyl]-amino}-piperidine-1-carboxylic acid tert-butyl ester, and purification method A, afforded the title compound as an off-white solid (70 mg, 100%); LCMS (method A), $R_T$=6.09 min, M+H$^+$=396; $^1$H NMR (DMSO-D$_6$, 300 MHz): 8.86 (s, 1H), 8.71 (br. s, 2H), 8.09 (d, J=2.7 Hz, 1H), 8.03 (d, J=7.30 Hz, 1H), 7.87 (d, J=8.6 Hz, 2H), 7.72 (d, J=8.5 Hz, 2H), 7.66 (d, J=2.6 Hz, 1H), 6.35 (br. s, 2H), 4.14-4.07 (m, 1H), 3.43-3.31 (m, 1H), 3.28-3.18 (m, 1H), 2.94-2.75 (m, 2H), 1.99-1.88 (m, 2H), 1.77-1.64 (m, 1H), 1.63-1.51 (m, 1H).

Example 3

1-(4-Cyanophenyl)-4-ureido-1H-pyrrole-3-carboxylic acid (S)-piperidin-3-ylamide—TFA

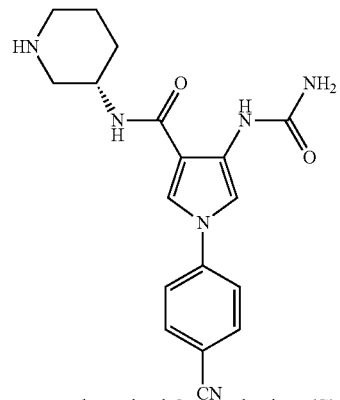 [SMILES: N#Cc1ccc(-n2cc(NC(N)=O)c(C(=O)N[C@H]3CCCNC3)c2)cc1]

Following general method 8, employing (S)-3-{[1-(4-cyanophenyl)-4-ureido-1H-pyrrole-3-carbonyl]-amino}-piperidine-1-carboxylic acid tert-butyl ester, and purification method A, afforded the title compound as an off-white solid (66 mg, 67%); LCMS (method A), $R_T$=4.96 min, M+H$^+$=353; $^1$H NMR (DMSO-D$_6$, 300 MHz): 8.86 (s, 1H), 8.66 (s, 2H), 8.11 (d, J=2.6 Hz, 1H), 8.04 (d, J=7.3 Hz, 1H), 8.01-7.94 (m, 2H), 7.71-7.64 (m, 3H), 6.39 (br. s, 2H), 4.17-4.02 (m, 1H), 3.27-3.13 (m, 2H), 2.84-2.74 (m, 2H), 2.02-1.84 (m, 2H), 1.79-1.48 (m, 2H).

Example 4

1-(4-Chloro-3-fluorophenyl)-4-ureido-1H-pyrrole-3-carboxylic acid (S)-piperidin-3-ylamide—TFA

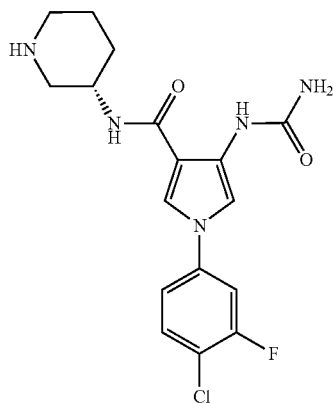 [SMILES: NC(=O)Nc1cn(-c2ccc(Cl)c(F)c2)cc1C(=O)N[C@H]1CCCNC1]

Following general method 8, employing (S)-3-{[1-(4-chloro-3-fluorophenyl)-4-ureido-1H-pyrrole-3-carbonyl]-amino}-piperidine-1-carboxylic acid tert-butyl ester, and purification method A, afforded the title compound as a white solid (146 mg, 68%); LCMS (method A), $R_T$=5.88 min, M+H$^+$=380; $^1$H NMR (DMSO-D$_6$, 300 MHz): 8.84 (s, 1H), 8.78 (s, 2H), 8.01 (d, J=3.7 Hz, 2H), 7.74-7.61 (m, 2H), 7.59 (d, J=2.6 Hz, 1H), 7.40 (dd, J=8.8, 2.5 Hz, 1H), 6.36 (br. s, 2H), 4.18-4.03 (m, 1H), 3.29-3.12 (m, 2H), 2.92-2.75 (m, 2H), 1.97-1.88 (m, 2H), 1.79-1.48 (m, 2H).

Example 5

1-(3-Fluoro-4-trifluoromethylphenyl)-4-ureido-1H-pyrrole-3-carboxylic acid (S)-piperidin-3-ylamide—TFA

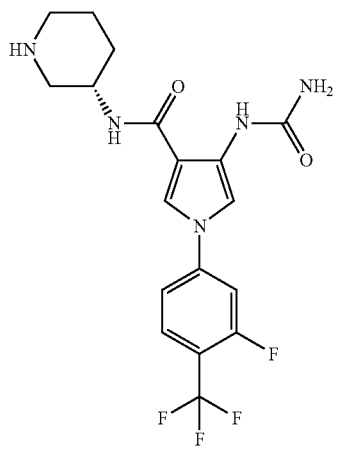 [SMILES: NC(=O)Nc1cn(-c2ccc(C(F)(F)F)c(F)c2)cc1C(=O)N[C@H]1CCCNC1]

Following general method 8, employing (S)-3-{[1-(3-fluoro-4-trifluoromethylphenyl)-4-ureido-1H-pyrrole-3-carbonyl]-amino}-piperidine-1-carboxylic acid tert-butyl ester, and purification method A, afforded the title compound as a white solid (120 mg, 100%); LCMS (method A), $R_T$=6.36 min, M+H$^+$=414; $^1$H NMR (DMSO-D$_6$, 300 MHz): 8.85 (s, 1H), 8.79 (s, 2H), 8.13 (d, J=2.6 Hz, 1H), 8.08 (d, J=7.3 Hz, 1H), 7.90 (t, J=8.4 Hz, 1H), 7.79-7.71 (m, 1H), 7.69 (d, J=2.6 Hz, 1H), 7.58-7.51 (m, 1H), 6.40 (br. s, 2H), 4.18-4.03 (m, 1H), 3.28-3.15 (m, 2H), 2.98-2.70 (m, 2H), 2.02-1.87 (m, 2H), 1.79-1.47 (m, 2H).

Example 6

1-(3-Chloro-4-trifluoromethylphenyl)-4-ureido-1H-pyrrole-3-carboxylic acid (S)-piperidin-3-ylamide—TFA

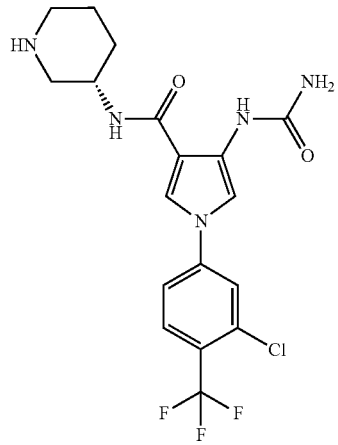 [SMILES: NC(=O)Nc1cn(-c2ccc(C(F)(F)F)c(Cl)c2)cc1C(=O)N[C@H]1CCCNC1]

Following general method 8, employing (S)-3-{[1-(3-chloro-4-trifluoromethyl phenyl)-4-ureido-1H-pyrrole-3-carbonyl]-amino}-piperidine-1-carboxylic acid tert-butyl ester, and purification method A, afforded the title compound as an off-white solid (115 mg, 51%); LCMS (method A), $R_T$=6.61 min, M+H$^+$=430; $^1$H NMR (DMSO-D$_6$, 300 MHz): 8.88 (s, 1H), 8.14 (d, J=2.7 Hz, 1H), 8.03 (d, J=7.4 Hz, 1H), 7.96 (d, J=8.8 Hz, 1H), 7.89 (d, J=2.1 Hz, 1H), 7.70-7.65 (m, 2H), 6.40 (br. s, 2H), 4.16-4.00 (m, 1H), 3.22-3.13 (m, 2H), 2.89-2.68 (m, 2H), 2.00-1.83 (m, 2H), 1.75-1.47 (m, 2H).

Example 7

1-(3-Fluorophenyl)-4-(3-methyl-ureido)-1H-pyrrole-3-carboxylic acid (S)-piperidin-3-ylamide

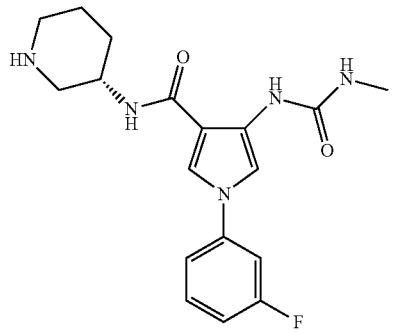 [SMILES: CNC(=O)Nc1cn(-c2cccc(F)c2)cc1C(=O)N[C@H]1CCCNC1]

Following general method 8, employing (S)-3-{[1-(3-fluorophenyl)-4-(3-methyl-ureido)-1H-pyrrole-3-carbonyl]-amino}-piperidine-1-carboxylic acid tert-butyl ester, and purification method D and then E, afforded the title compound as a white solid (105 mg, 79%); LCMS (method A), R$_T$=5.10 min, M+H$^+$=360; $^1$H NMR (CDCl$_3$, 300 MHz): 9.15 (s, 1H), 7.63 (d, J=2.5 Hz, 1H), 7.42-7.31 (m, 2H), 7.23-7.09 (m, 2H), 6.95 (td, J=8.3, 2.4 Hz, 1H), 6.74 (d, J=8.4 Hz, 1H), 4.92-4.82 (m, 1H), 4.20-4.09 (m, 1H), 3.06 (dd, J=12.0, 3.2 Hz, 1H), 2.91-2.74 (m, 6H), 1.85-1.67 (m, 3H), 1.65-1.50 (m, 1H).

Example 8

4-(3-Ethyl-ureido)-1-(3-fluorophenyl)-1H-pyrrole-3-carboxylic acid (S)-piperidin-3-ylamide—TFA

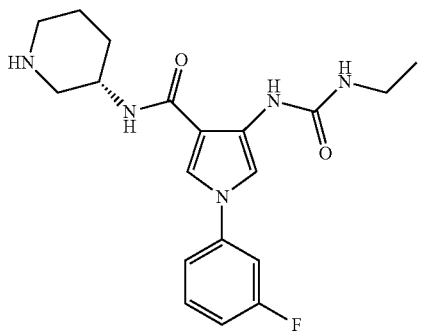 [SMILES: CCNC(=O)Nc1cn(-c2cccc(F)c2)cc1C(=O)N[C@H]1CCCNC1]

Following general method 8, employing (S)-3-{[4-(3-ethyl-ureido)-1-(3-fluorophenyl)-1H-pyrrole-3-carbonyl]amino}-piperidine-1-carboxylic acid tert-butyl ester, and purification method D and then E, afforded the title compound as a white solid (144 mg, 71%); LCMS (method A), R$_T$=5.85 min, M+H$^+$=374; $^1$H NMR (CD$_3$OD, 300 MHz): 7.78 (d, J=2.1 Hz, 1H), 7.54-7.46 (m, 2H), 7.34-7.24 (m, 2H), 7.07-7.05 (m, 1H), 4.21 (m, 1H), 3.52 (m, 1H), 3.35 (m, 1H), 3.22 (q, J=7.2 Hz, 2H), 3.09-2.84 (m, 2H), 2.16-1.98 (m, 2H), 1.94-1.62 (m, 2H), 1.17 (t, J=7.2 Hz, 3H).

Example 9

1-(3-Fluorophenyl)-4-(3-isopropyl-ureido)-1H-pyrrole-3-carboxylic acid (S)-piperidin-3-ylamide—TFA

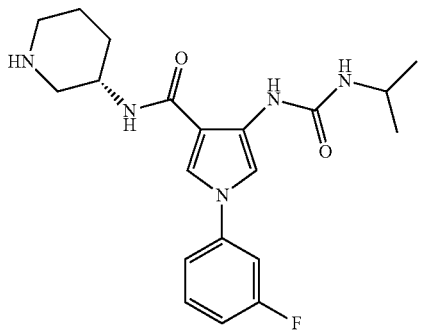 [SMILES: CC(C)NC(=O)Nc1cn(-c2cccc(F)c2)cc1C(=O)N[C@H]1CCCNC1]

Following general method 8, (S)-3-{[1-(3-fluorophenyl)-4-(3-isopropyl-ureido)-1H-pyrrole-3-carbonyl]-amino-piperidine-1-carboxylic acid tert-butyl ester, and purification method A, afforded the title compound as a cream solid (80 mg, 100%); LCMS (method A), R$_T$=6.17 min, M+H$^+$=388; $^1$H NMR (CDCl$_3$, 300 MHz): 9.51-9.22 (m, 2H), 9.09 (m, 1H), 7.80 (m, 1H), 7.67 (s, 1H), 7.49 (d, J=2.4 Hz, 1H), 7.34 (m, 1H), 7.20-7.04 (m, 2H), 6.95 (td, J=8.3, 2.4 Hz, 1H), 4.47 (m, 1H), 3.83 (m, 1H), 3.35-3.09 (m, 3H), 2.98 (m, 1H), 2.13 (m, 1H), 1.98-1.74 (m, 3H), 1.22 (d, J=6.3 Hz, 6H).

Example 10

4-(3-Cyclopropylmethyl-ureido)-1-(3-fluorophenyl)-1H-pyrrole-3-carboxylic acid (S)-piperidin-3-ylamide

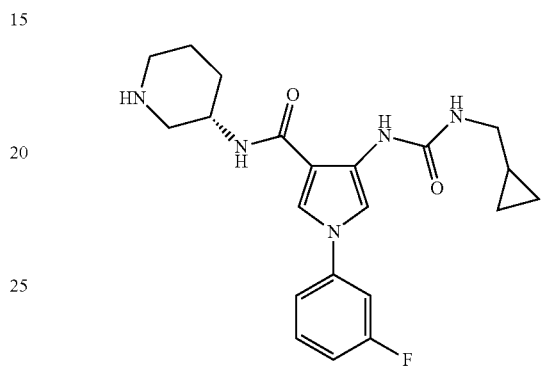

Following general method 8, employing (S)-3-{[4-(3-cyclopropylmethyl-ureido)-1-(3-fluorophenyl)-1H-pyrrole-3-carbonyl]-amino}-piperidine-1-carboxylic acid tert-butyl ester, and purification method B, afforded the title compound as a white solid (40 mg, 50% over 2 steps); LCMS (method A), R$_T$=6.43 min, M+H$^+$=400; $^1$H NMR (CDCl$_3$, 300 MHz): 9.07 (s, 1H), 7.60 (s, 1H), 7.49 (s, 1H), 7.35-7.26 (m, 1H), 7.15 (d, J=8.7 Hz, 2H), 6.90 (t, J=8.3 Hz, 1H), 5.32 (s, 1H), 4.88-4.24 (br. s, 1H), 4.24-4.09 (m, 1H), 3.09-2.97 (m, 3H), 2.96-2.66 (m, 3H), 1.91-1.49 (m, 4H), 1.04-0.90 (m, 1H), 0.51-0.39 (m, 2H), 0.22-0.11 (m, 2H).

Example 11

1-(3-Fluorophenyl)-4-[3-(2-methoxy-ethyl)-ureido]-1H-pyrrole-3-carboxylic acid (S)-piperidin-3-ylamide

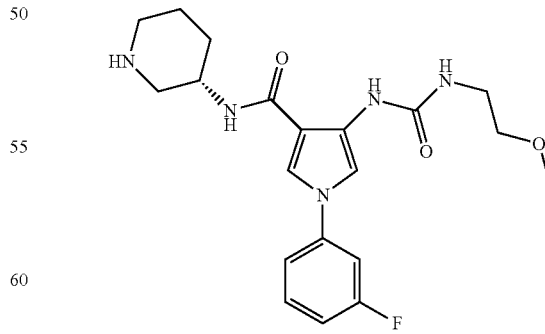

Following general method 8, employing (S)-3-({1-(3-fluorophenyl)-4-[3-(2-methoxy-ethyl)-ureido]-1H-pyrrole-3-carbonyl}-amino)-piperidine-1-carboxylic acid tert-butyl ester, and purification method B, afforded the title compound as a white solid (38 mg, 47% over 2 steps); LCMS (method A), $R_T$=5.83 min, M+H$^+$=404; $^1$H NMR (CDCl$_3$, 300 MHz): 9.13 (s, 1H), 7.60 (d, J=2.5 Hz, 1H), 7.46 (d, J=2.5 Hz, 1H), 7.38-7.24 (m, 1H), 7.19-7.14 (m, 1H), 7.14-7.08 (m, 1H), 6.97-6.89 (m, 2H), 5.45 (s, 1H), 4.21-4.07 (m, 1H), 3.58-3.40 (m, 4H), 3.35 (s, 3H), 3.12-3.00 (m, 1H), 2.88-2.76 (m, 3H), 1.87-1.69 (m, 3H), 1.63-1.50 (m, 1H).

Example 12

4-(3-Cyclopropyl-ureido)-1-(3-fluorophenyl)-1H-pyrrole-3-carboxylic acid (S)-piperidin-3-ylamide

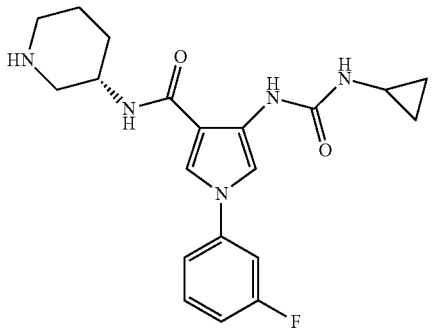 [SMILES: O=C(Nc1cn(-c2cccc(F)c2)cc1C(=O)N[C@H]1CCCNC1)NC1CC1]

Following general method 8, employing (S)-3-{[4-(3-cyclopropyl-ureido)-1-(3-fluorophenyl)-1H-pyrrole-3-carbonyl]-amino}-piperidine-1-carboxylic acid tert-butyl ester (94 mg, 0.19 mmol), and purification methods D and then E, afforded the title compound as a white solid (19 mg, 26%); LCMS (method A), $R_T$=5.83 min, M+H$^+$=386; $^1$H NMR (CD$_3$OD, 300 MHz): 7.83 (d, J=2.6 Hz, 1H), 7.56 (d, J=2.6 Hz, 1H), 7.52-7.43 (m, 1H), 7.34-7.29 (m, 1H), 7.28 (dt, J=10.2, 2.3 Hz, 1H), 7.07-7.01 (m, 1H), 4.02-3.93 (m, 1H), 3.14 (dd, J=12.2, 3.9 Hz, 1H), 2.92 (dt, J=12.7, 3.7 Hz, 1H), 2.62-2.49 (m, 3H), 2.04-1.96 (m, 1H), 1.83-1.73 (m, 1H), 1.67-1.51 (m, 2H), 0.83 (d, J=6.7 Hz, 2H), 0.63-0.54 (m, 2H).

Example 13

1-(3-Fluorophenyl)-4-[3-(2-hydroxyethyl)-ureido]-1H-pyrrole-3-carboxylic acid (S)-piperidin-3-ylamide TFA

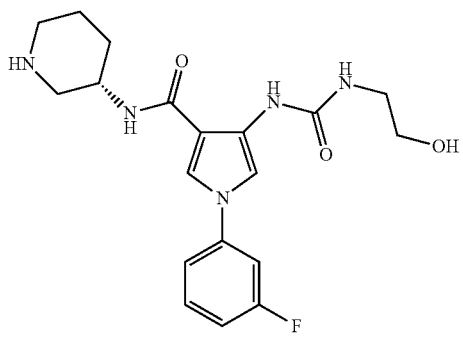 [SMILES: O=C(NCCO)Nc1cn(-c2cccc(F)c2)cc1C(=O)N[C@H]1CCCNC1]

Following general method 8, employing (S)-3-({1-(3-fluorophenyl)-4-[3-(2-hydroxyethyl)-ureido]-1H-pyrrole-3-carbonyl}-amino)-piperidine-1-carboxylic acid tert-butyl ester (60 mg, 0.12 mmol), and purification method A, afforded the title compound as a white solid (23 mg, 48%); LCMS (method A), $R_T$=2.12 min, M+H$^+$=390; $^1$H NMR (CD$_3$OD, 400 MHz): 7.81-7.79 (m, 1H), 7.54-7.42 (m, 1H), 7.32-7.29 (m, 1H), 7.26 (dt, J=10.2, 2.3 Hz, 1H), 7.04 (tdd, J=8.3, 2.4, 0.8 Hz, 1H), 4.24 (tt, J=10.2, 3.9 Hz, 1H), 3.64 (t, J=5.7 Hz, 2H), 3.51 (dd, J=12.3, 4.0 Hz, 1H), 3.32-3.29 (m, 3H), 3.03-2.90 (m, 2H), 2.11-2.03 (m, 2H), 1.92-1.78 (m, 1H), 1.77-1.66 (m, 1H).

Example 14

1-(3-Fluorophenyl)-4-(3-propyl-ureido)-1H-pyrrole-3-carboxylic acid (S)-piperidin-3-ylamide TFA

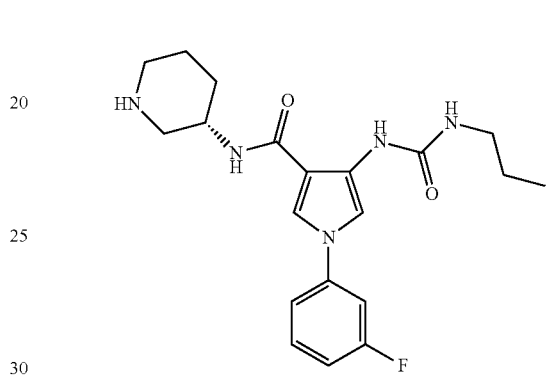

Following general method 8, employing (S)-3-({1-(3-fluorophenyl)-4-[3-propylureido]-1H-pyrrole-3-carbonyl}-amino)-piperidine-1-carboxylic acid tert-butyl ester (100 mg, 0.20 mmol), and purification method A, afforded the title compound as a white solid (60 mg, 76%); LCMS (method A), $R_T$=2.31 min, M+H$^+$=388; $^1$H NMR (CD$_3$OD, 400 MHz): 7.80 (t, J=2.9 Hz, 1H), 7.51-7.42 (m, 2H), 7.31-7.22 (m, 2H), 7.03 (tdd, J=8.3, 2.4, 0.8 Hz, 1H), 4.29-4.20 (m, 1H), 3.55-3.49 (m, 1H), 3.33-3.30 (m, 1H), 3.16 (t, J=7.0 Hz, 2H), 3.05-2.93 (m, 2H), 2.12-2.04 (m, 2H), 1.93-1.79 (m, 1H), 1.79-1.67 (m, 1H), 1.62-1.51 (m, 2H), 0.97 (t, J=7.4 Hz, 3H).

Example 15

1-(3-Fluorophenyl)-4-[3-(3-hydroxypropyl)-ureido]-1H-pyrrole-3-carboxylic acid (S)-piperidin-3-ylamide TFA

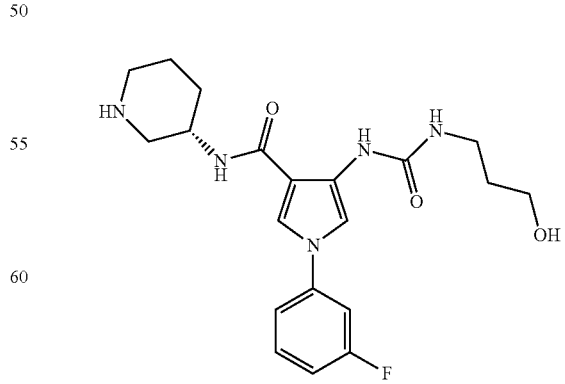

Following general method 8, employing (S)-3-({1-(3-fluorophenyl)-4-[3(3-hydroxypropyl)-ureido]-1H-pyrrole-3-carbonyl}-amino)-piperidine-1-carboxylic acid tert-butyl ester (70 mg, 0.14 mmol), and purification method A, afforded the title compound as a white solid (18 mg, 32%); LCMS (method A), $R_T$=2.11 min, M+H$^+$=404; $^1$H NMR (CD$_3$OD, 400 MHz): 7.80-7.79 (m, 1H), 7.53 (d, J=2.5 Hz, 1H), 7.48 (td, J=8.2, 6.2 Hz, 1H), 7.32-7.29 (m, 1H), 7.26 (dt, J=10.2, 2.3 Hz, 1H), 7.04 (tdd, J=8.3, 2.4, 0.8 Hz, 1H), 4.24 (tt, J=10.2, 3.9 Hz, 1H), 3.64 (t, J=6.3 Hz, 2H), 3.51 (dd, J=12.3, 4.0 Hz, 1H), 3.32-3.29 (m, 2H), 3.31-3.26 (m, 2H), 3.08-2.89 (m, 2H), 2.11-2.02 (m, 2H), 1.93-1.79 (m, 1H), 1.76 (t, J=6.5 Hz, 2H).

Example 16

1-(3-Fluorophenyl)-4-[3-(3-methoxy-propyl)-ureido]-1H-pyrrole-3-carboxylic acid (S)-piperidin-3-ylamide TFA

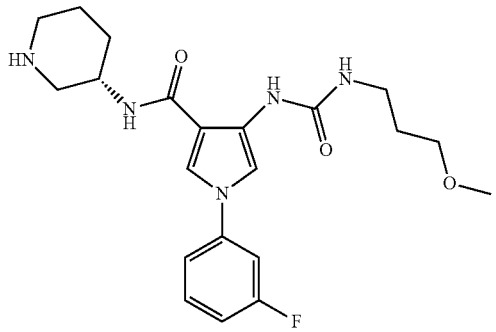 [SMILES: COCCCNC(=O)Nc1cn(-c2cccc(F)c2)cc1C(=O)N[C@H]1CCCNC1]

Following general method 8, employing (S)-3-({1-(3-fluorophenyl)-4-[3-(3-methoxypropyl)-ureido]-1H-pyrrole-3-carbonyl}-amino)-piperidine-1-carboxylic acid tert-butyl ester (100 mg, 0.19 mmol), and purification method A, afforded the title compound as a white solid (75 mg, 92%); LCMS (method A), $R_T$=2.21 min, M+H$^+$=418; $^1$H NMR (CDCl$_3$, 300 MHz): 9.52 (s, 1H), 9.21 (s, 1H), 8.97 (s, 1H), 7.61-7.54 (m, 2H), 7.34 (td, J=8.2, 6.2 Hz, 1H), 7.23-7.16 (m, 1H), 7.14 (dt, J=9.9, 2.3 Hz, 1H), 6.94 (td, J=8.2, 2.4 Hz, 1H), 5.80 (s, 1H), 4.43 (s, 1H), 3.45 (t, J=6.0 Hz, 2H), 3.38-3.30 (m, 3H), 3.29 (s, 3H), 3.02 (t, J=10.6 Hz, 1H), 2.90 (q, J=10.5 Hz, 1H), 2.30-2.12 (m, 3H), 1.97-1.82 (m, 1H), 1.85-1.75 (m, 3H).

Example 17

4-[3-(2-Fluoroethyl)-ureido]-1-(3-fluoro-phenyl)-1H-pyrrole-3-carboxylic acid (S)-piperidin-3-ylamide TFA

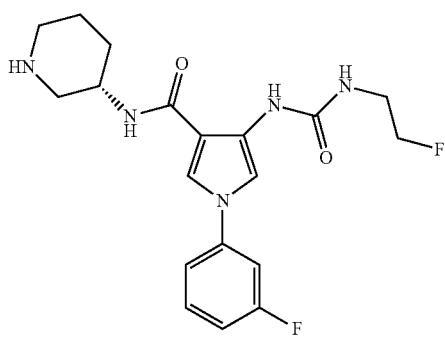 [SMILES: O=C(NCCF)Nc1cn(-c2cccc(F)c2)cc1C(=O)N[C@H]1CCCNC1]

Following general method 8, employing (S)-3-({1-(3-fluorophenyl)-4-[3-(2-fluoroethyl)-ureido]-1H-pyrrole-3-carbonyl}-amino)-piperidine-1-carboxylic acid tert-butyl ester (80 mg, 0.16 mmol), and purification method A, afforded the title compound as a white solid (45 mg, 70%); LCMS (method A), $R_T$=2.20 min, M+H$^+$=392; $^1$H NMR (CD$_3$OD, 300 MHz): 7.78 (s, 1H), 7.56-7.46 (m, 2H), 7.35-7.26 (m, 2H), 7.06 (tdd, J=8.3, 2.4, 0.9 Hz, 1H), 4.49-4.38 (m, 2H), 4.28-4.18 (m, 1H), 3.56-3.49 (m, 2H), 3.46 (t, J=5.0 Hz, 1H), 3.37-3.31 (m, 1H), 3.04-2.88 (m, 2H), 2.13-2.04 (m, 2H), 1.91-1.78 (m, 1H), 1.77-1.66 (m, 1H).

Example 18

4-[3-(2,2-Difluoroethyl)-ureido]-1-(3-fluoro-phenyl)-1H-pyrrole-3-carboxylic acid (S)-piperidin-3-ylamide TFA

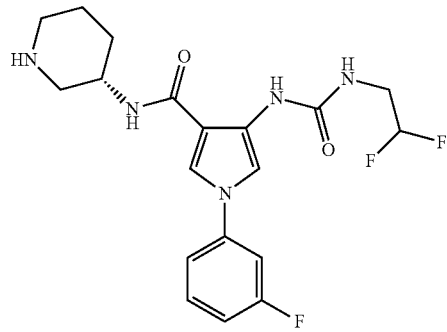 [SMILES: O=C(NCC(F)F)Nc1cn(-c2cccc(F)c2)cc1C(=O)N[C@H]1CCCNC1]

Following general method 8, employing (S)-3-({1-(3-fluorophenyl)-4-[3-(2,2-difluoroethyl)-ureido]-1H-pyrrole-3-carbonyl}-amino)-piperidine-1-carboxylic acid tert-butyl ester (100 mg, 0.20 mmol), and purification method A, afforded the title compound as a white solid (55 mg, 68%); LCMS (method A), $R_T$=2.24 min, M+H$^+$=410; $^1$H NMR (DMSO-d$_6$, 400 MHz): 9.04 (s, 1H), 8.72 (s, 2H), 8.03-7.96 (m, 2H), 7.71 (t, J=5.9 Hz, 1H), 7.61 (d, J=2.5 Hz, 1H), 7.59-7.51 (m, 1H), 7.43-7.35 (m, 2H), 7.15 (td, J=8.4, 2.4 Hz, 1H), 6.02 (tt, J=56.0, 3.8 Hz, 1H), 4.15-4.06 (m, 1H), 3.54-3.41 (m, 2H), 3.38-3.29 (m, 1H), 3.28-3.17 (m, 1H), 2.98-2.70 (m, 2H), 1.99-1.89 (m, 2H), 1.76-1.63 (m, 1H), 1.64-1.54 (m, 1H).

Example 19

1-(3-Fluorophenyl)-4-[3-(2,2,2-trifluoroethyl)-ureido]-1H-pyrrole-3-carboxylic acid (S)-piperidin-3-ylamide—TFA

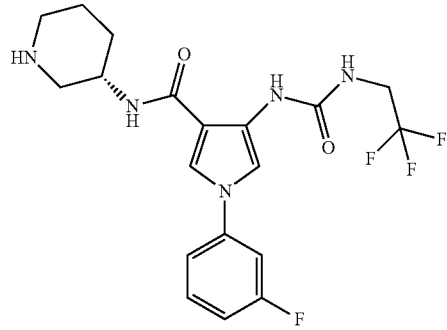 [SMILES: O=C(NCC(F)(F)F)Nc1cn(-c2cccc(F)c2)cc1C(=O)N[C@H]1CCCNC1]

Following general method 8, employing (S)-3-({1-(3-fluorophenyl)-4-[3-(2,2,2-trifluoroethyl)-ureido]-1H-pyrrole-3-carbonyl}-amino)-piperidine-1-carboxylic acid tert-butyl ester (70 mg, 0.13 mmol), and purification method A, afforded the title compound as a white solid (25 mg, 44%); LCMS (method A), $R_T$=2.37 min, M+H$^+$=428; $^1$H NMR (400 MHz, DMSO-d$_6$): 9.13 (s, 1H), 8.71 (s, 2H), 8.04-7.97 (m, 3H), 7.62 (d, J=2.5 Hz, 1H), 7.59-7.51 (m, 1H), 7.44-7.36 (m, 2H), 7.16 (td, J=8.4, 2.4 Hz, 1H), 4.16-4.06 (m, 1H), 3.96-3.84 (m, 2H), 3.38-3.29 (m, 1H), 3.23 (d, J=12.2 Hz, 1H), 2.94-2.74 (m, 2H), 1.97-1.88 (m, 2H), 1.75-1.66 (m, 1H), 1.62-1.54 (m, 1H).

Example 20

1-(4-Chloro-3-fluoro-phenyl)-4-(3-ethyl-ureido)-1H-pyrrole-3-carboxylic acid (S)-piperidin-3-ylamide

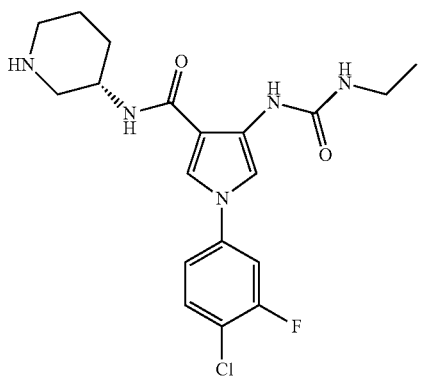 [SMILES: CCNC(=O)Nc1cn(-c2ccc(Cl)c(F)c2)cc1C(=O)N[C@H]1CCCNC1]

Following general method 8, employing (S)-3-{[4-(3-ethyl-ureido)-1-(4-chloro-3-fluorophenyl)-1H-pyrrole-3-carbonyl]-amino}-piperidine-1-carboxylic acid tert-butyl ester, and purification method D, afforded the title compound as a white solid (70 mg, 40%); LCMS (method A), $R_T$=6.49 min, M+H$^+$=408; $^1$H NMR (DMSO-D$_6$, 400 MHz): 8.96 (s, 1H), 8.04 (d, J=2.6 Hz, 1H), 7.74-7.62 (m, 3H), 7.58 (d, J=2.6 Hz, 1H), 7.41-7.37 (m, 1H), 7.15 (t, J=5.5 Hz, 1H), 3.85-3.74 (m, Hi), 3.12-2.98 (m, 3H), 2.83 (dt, J=12.1, 3.3 Hz, 1H), 2.48-2.44 (m, 1H), 2.40 (dd, J=11.9, 9.5 Hz, 1H), 1.90-1.83 (m, 1H), 1.72-1.64 (m, 1H), 1.48-1.38 (m, 2H), 1.03 (t, J=7.2 Hz, 3H).

Example 21

1-(3-Fluorophenyl)-4-ureido-1H-pyrrole-3-carboxylic acid ((S)-1-methyl-piperidin-3-yl)-amide

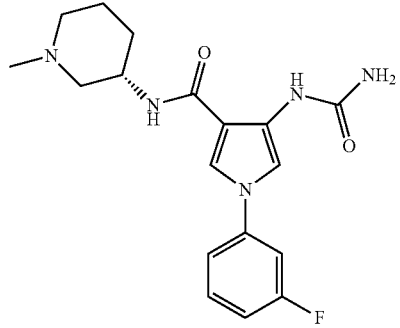 [SMILES: CN1CCC[C@H](NC(=O)c2cn(-c3cccc(F)c3)cc2NC(N)=O)C1]

To a solution of (S)-1-methyl-piperidin-3-yl amine (120 mg, 1.05 mmol) in THF (8.0 mL), under nitrogen, was added 2N trimethylaluminium in hexanes (1.0 mL, 2.0 mmol), and the reaction mixture was allowed to stir at room temperature for 1.5 hours. After this time, a THF (5.0 mL) solution of 1-(3-fluorophenyl)-4-ureido-1H-pyrrole-3-carboxylic acid ethyl ester (291 mg, 1.0 mmol), was added and the reaction mixture was heated at 65-70° C. for a period of 18 hours. After this time, the reaction mixture was allowed to cool to room temperature and was then quenched by addition of a saturated solution of Rochelle's salt. After 0.5 hours, the mixture was extracted with DCM (3×10 mL) and EtOAc (1×10 mL). The combined organic layer was dried (MgSO$_4$) and concentrated in vacuo. The resultant residue was then purified by flash chromatography (silica, 5 g column, Isolute, 0-20% MeOH in DCM) to afford the title compound (60 mg, 0.17 mmol, 17%). LCMS (method A), $R_T$=5.13 min, M+H$^+$=360; $^1$H NMR (DMSO-D$_6$, 400 MHz): 8.97 (s, 1H), 8.05 (d, J=2.6 Hz, 1H), 7.68 (d, J=7.8 Hz, 1H), 7.56 (d, J=2.6 Hz, 1H), 7.55-7.48 (m, 1H), 7.39 (dt, J=10.6, 2.3 Hz, 1H), 7.36-7.33 (m, 1H), 7.12 (td, J=8.5, 2.4 Hz, 1H), 6.29 (s, 2H), 3.95-3.88 (m, 1H), 2.85-2.77 (m, 1H), 2.65-2.57 (m, 1H), 2.18 (s, 3H), 1.92-1.73 (m, 3H), 1.74-1.67 (m, 1H), 1.58-1.46 (m, 1H), 1.33-1.19 (m, 1H).

We claim:
1. A compound of Formula (I):

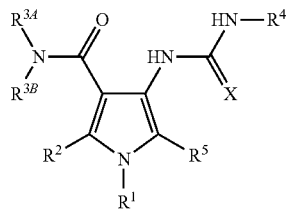

R[1] is phenyl or heteroaryl wherein said phenyl and heteroaryl is optionally substituted with one to five groups independently selected from halo, CN, and CF$_3$;
R[2] is H;
R$^{3A}$ and R$^{3B}$ are independently H, cycloalkyl, or heterocyclyl, wherein said cycloalkyl, and heterocyclyl are optionally substituted with one to five alkyl groups;
X is O; and
R[4] is H, C$_1$-C$_3$ alkyl, C$_3$-C$_5$ cycloalkyl, wherein said alkyl is optionally substituted with one or more groups selected from OH, O(C$_1$-C$_2$ alkyl), fluoro and C$_3$-C$_5$ cycloalkyl;
R[5] is H.

2. The compound of claim 1 wherein R[1] is phenyl substituted with one to three groups independently selected from halo, CN and CF$_3$.
3. The compound of claim 2 wherein R$^{3A}$ is H.
4. The compound of claim 3 wherein R$^{3B}$ is H, cycloalkyl or heterocyclyl, wherein said cycloalkyl and heterocyclyl are optionally substituted with one to three alkyl groups.
5. The compound of claim 4 wherein R$^{3B}$ is 4-7 membered monocyclic or 8-10 membered bicyclic saturated heterocyclyl.
6. The compound of claim 5 wherein R$^{3B}$ is piperdinyl.
7. The compound of claim 6 wherein R[4] is H, CH$_3$, CH$_2$CH$_3$, n-propyl, i-propyl, CH$_2$CH$_2$OH, CH$_2$CH$_2$OCH$_3$, CH$_2$CH$_2$CH$_2$OH, CH$_2$CH$_2$CH$_2$OCH$_3$, cyclopropyl, CH$_2$-cyclopropyl, CH$_2$CH$_2$F, CH$_2$CHF$_2$, or CH$_2$CF$_3$.
8. A pharmaceutical composition comprising a compound of claim 1 and a pharmaceutically acceptable carrier.
9. The pharmaceutical composition of claim 8, further comprising a second chemotherapeutic agent.
10. The pharmaceutical composition of claim 9, wherein said second chemotherapeutic agent is a DNA damaging agent.
11. The compound of claim 1, wherein it is selected from the group consisting of:

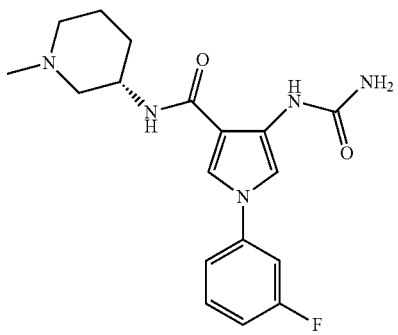

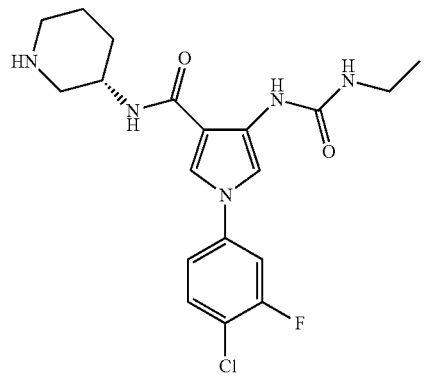

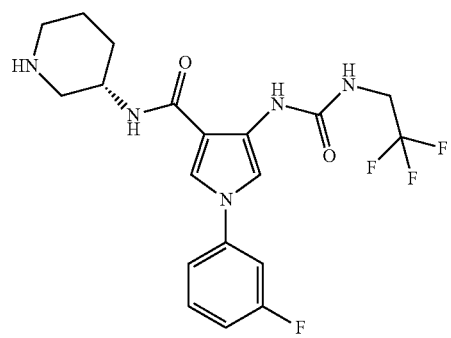

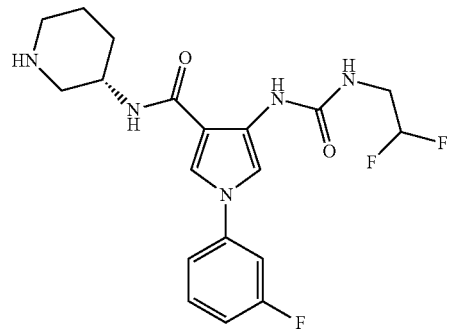

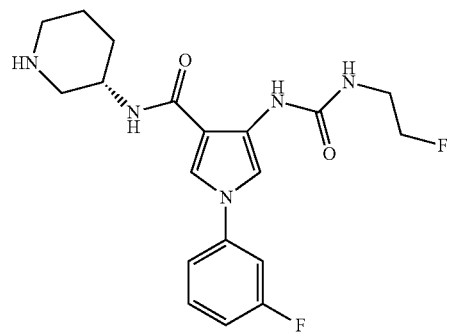

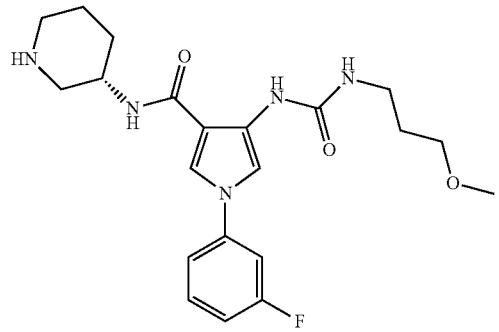

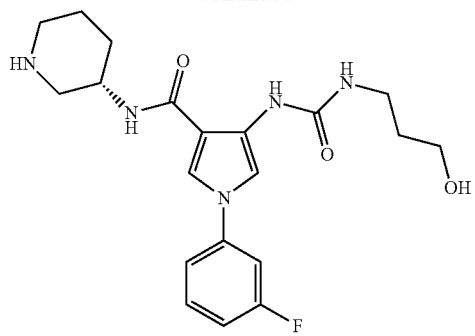
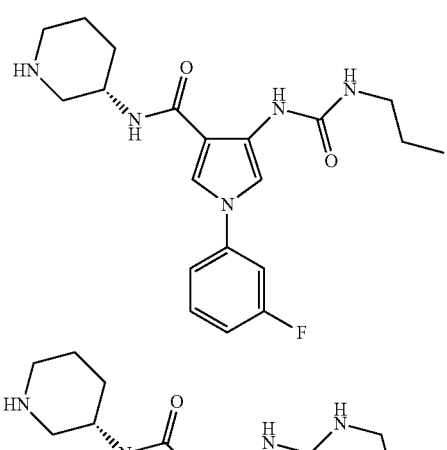
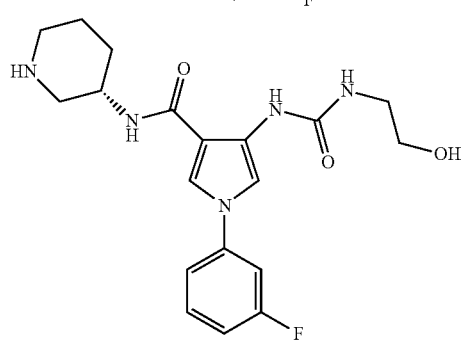
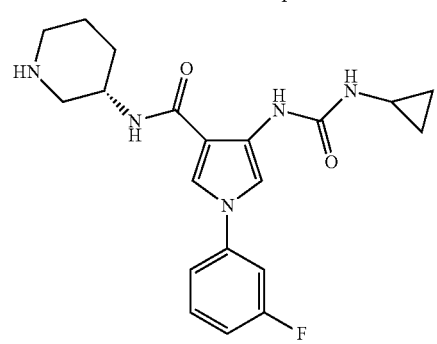
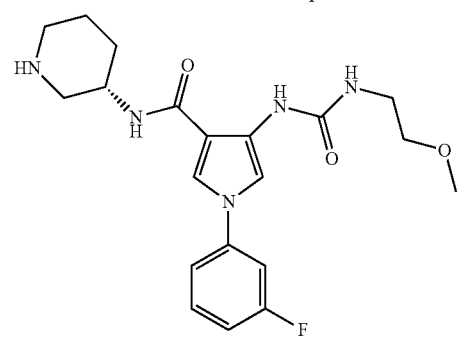
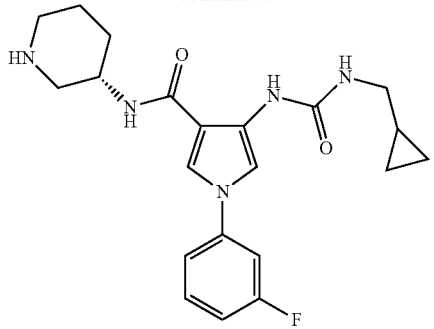
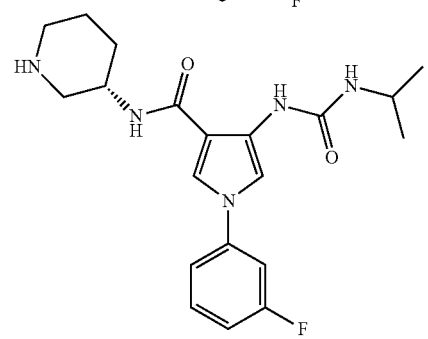
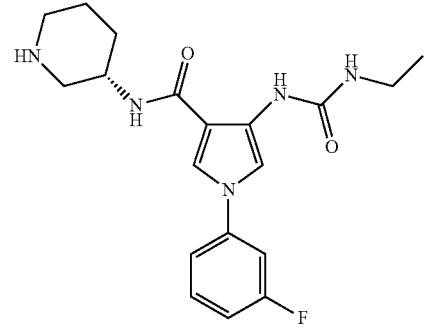
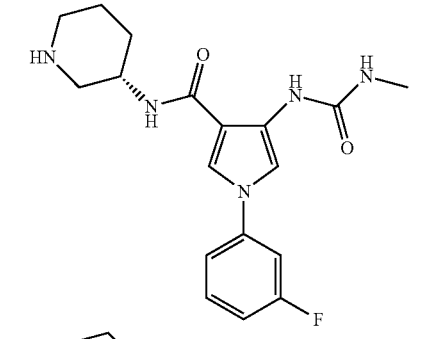
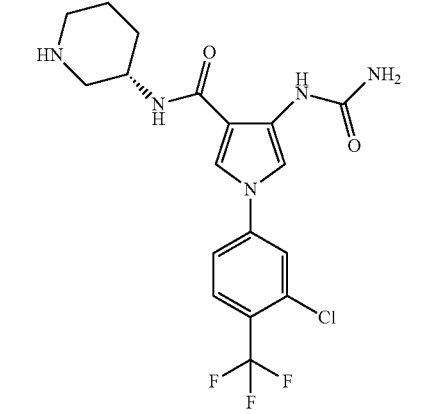

61
-continued
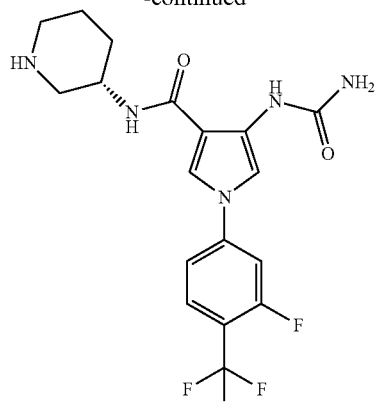
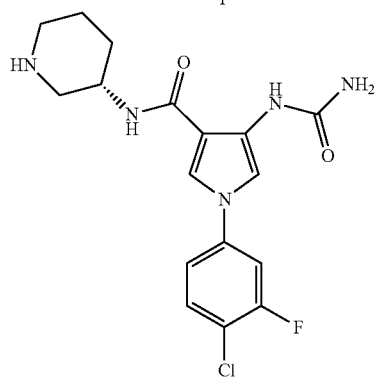
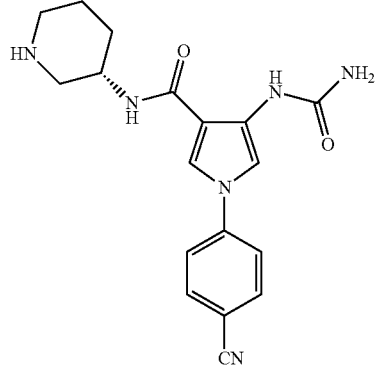
62
-continued
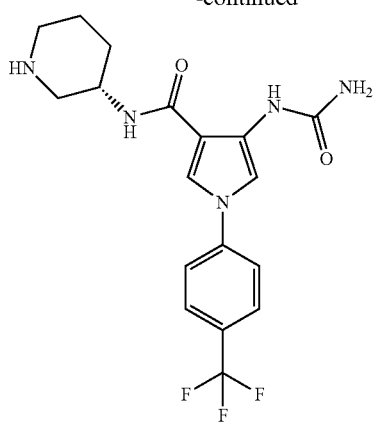
and
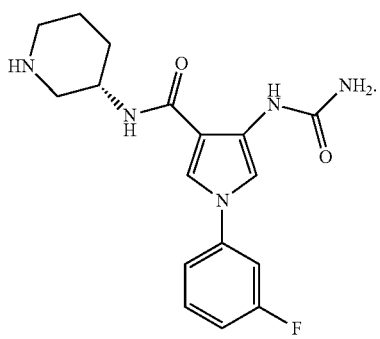
* * * * *